United States Patent
Chen et al.

(10) Patent No.: US 9,682,040 B2
(45) Date of Patent: *Jun. 20, 2017

(54) PHOSPHOLIPID DEPOT

(71) Applicant: Dr. Reddy's Laboratories Ltd., Hyderabad, A.P. (IN)

(72) Inventors: Hailiang Chen, San Diego, CA (US); Andrew Xian Chen, San Diego, CA (US); Dushyanth Surakanti, Somerset, NJ (US); Franklin Okumu, Oakland, CA (US)

(73) Assignee: Dr. Reddy's Laboratories Ltd., Hyderabad, Telangana (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,949

(22) Filed: Nov. 10, 2016

(65) Prior Publication Data

US 2017/0056326 A1    Mar. 2, 2017

Related U.S. Application Data

(63) Continuation of application No. 14/793,552, filed on Jul. 7, 2015, now Pat. No. 9,522,169, which is a continuation of application No. 13/242,778, filed on Sep. 23, 2011, now Pat. No. 9,132,144, which is a continuation of application No. PCT/US2010/061015, filed on Dec. 17, 2010.

(60) Provisional application No. 61/375,502, filed on Aug. 20, 2010.

(51) Int. Cl.
| | |
|---|---|
| *A61K 38/14* | (2006.01) |
| *A61K 31/7036* | (2006.01) |
| *A61K 9/19* | (2006.01) |
| *A61K 9/24* | (2006.01) |
| *A61K 9/16* | (2006.01) |
| *A61K 9/107* | (2006.01) |
| *A61K 47/24* | (2006.01) |
| *A61K 47/44* | (2017.01) |
| *A61K 47/10* | (2017.01) |

(52) U.S. Cl.
CPC .......... *A61K 9/107* (2013.01); *A61K 31/7036* (2013.01); *A61K 38/14* (2013.01); *A61K 47/10* (2013.01); *A61K 47/24* (2013.01); *A61K 47/44* (2013.01)

(58) Field of Classification Search
CPC .... A61K 9/0019; A61K 9/0024; A61K 36/41; A61K 47/24; A61K 9/70; A61K 31/685; A61K 38/212; A61K 38/25; A61K 47/12; A61K 47/14; A61K 47/183; A61K 47/26; A61K 47/28; A61K 9/0014; A61K 9/0029
See application file for complete search history.

(56) References Cited

U.S. PATENT DOCUMENTS 9,132,144 B2 *   9/2015   Chen ................... A61K 9/0019

* cited by examiner

*Primary Examiner* — Audrea Buckley
(74) *Attorney, Agent, or Firm* — Stites & Harbison, PLLC; Mandy Wilson Decker; Sean P. Ritchie

(57) ABSTRACT

The present invention provides a clear depot comprising at least one hydrophilic water-soluble pharmaceutically active agent selected from the group consisting of vancomycin, gentamicin, a pharmaceutically acceptable salt thereof and a mixture thereof, water, a phospholipid, an oil, optionally a pH adjusting agent, and a viscosity modifying agent selected from the group consisting of ethanol, isopropanol, and a mixture thereof, wherein the water present in the depot is no more than about 4 wt % relative to the total weight of the depot and the depot has a pH of between about 3 and about 6, method of making and administering same.

45 Claims, 14 Drawing Sheets

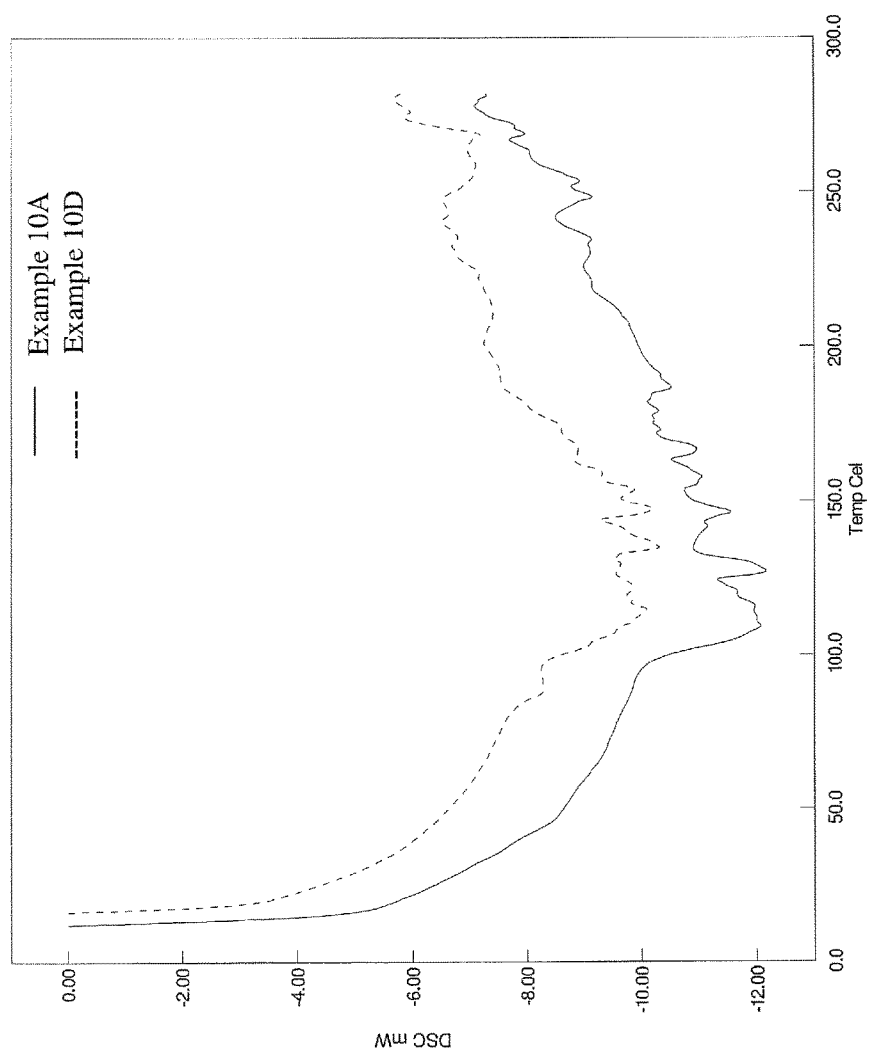

PHOSPHOLIPID DEPOT

CROSS-REFERENCE TO RELATED APPLICATION

This application is a continuation of U.S. patent application Ser. No. 14/793,552, filed Jul. 7, 2015, which is a continuation of U.S. patent application Ser. No. 13/242,778, filed Sep. 23, 2011, which is a continuation of International application No. PCT/US2010/061015, filed Dec. 17, 2010, which claims the benefit of the filing date of U.S. Provisional Patent Application No. 61/375,502 filed Aug. 20, 2010, each of which are incorporated herein by reference in their entirety.

BACKGROUND OF THE INVENTION

A depot is a way of administering an active ingredient into the body of a patient for systemic or local action. It is generally administered by subcutaneous or intramuscular injection or instillation into other body tissues, vessels or cavities. A depot can also be applied to a wound before it is staunched, stitched, bandaged or otherwise closed. Unlike removable depots, biodegradable depots disintegrate or degrade within a pre-defined time, typically after the entrapped active pharmaceutical ingredient has been delivered. In other constructs, the biodegradable injectable depot releases its active pharmaceutical ingredient roughly simultaneously with, or as a function of, its gradual degradation. A key advantage of certain biodegradable delivery depots is their ability to deliver medication directly to the intended site of action providing elevated local concentrations of medication when compared to systemic levels.

Depots can also modulate delivery of medication to enable various release profiles. The release profile could be immediate release (burst) followed by a steady state, could be, among others, "zero order" or constant rate of delivery, could provide a slow rise to steady state, or could even provide for a delayed release. In addition, depots have the advantage of allowing release over an extended period of time, with a single administration. Blood levels are not compromised by, for example, patient compliance issues.

Depots can be comprised of particulate systems such as microsphere-based depots and nanosphere-based depots, or can also be comprised of a biodegradable gel, typically made from soluble matrix formers (polymers, lipids, carbohydrates) and either an organic solvent or a mixture of water miscible and non-miscible solvents.

Phospholipids have been used to prepare depots comprising a lipophilic pharmacological active agent. Phospholipids are soluble in oils or organic solvents but insoluble in water. To form a depot, a high concentration of depot-forming phospholipids is often required. This can impact the volume and viscosity of the resulting depot and, accordingly, currently available phospholipid depots can be very difficult to inject through a conventional needle or a syringe. References describing phospholipids-based formulations include WO 89/00077, WO 02/32395, EP 0282405 and U.S. Pat. Nos. 5,863,549, 4,252,793, 5,660,854, 5,693,337, and Wang et al., *Lyophilization Of Water-In-Oil Emulsions To Prepare Phospholipid-Based Anhydrous Reverse Micelles For Oral Peptide Delivery*, 39 European Journal of Pharmaceutical Sciences, at 373-79 (2010).

Vancomycin is a glycopeptide antibiotic used in the prophylaxis and treatment of infections caused by Gram-positive bacteria. It is generally the drug of choice for serious infection and endocarditis caused by *S. aureus*, coagulase-negative staphylococci, streptococcus pneumoniase, β-hemolytic streptococci, corynebacterium group JK, viridans streptococci, or enterococci when β-lactams cannot be used because of drug allergy or resistance. Vancomycin can be combined with other antimicrobials when treating, inter alia, methicillin-resistant coagulase-negative staphylococcal prosthetic valve endocarditis, and enterococcal endocarditis. It has also been used as an alternative agent for pneumococcal meningitis caused by strains with reduced penicillin sensitivity. Vancomycin has been used in cardiac and vascular surgery to prevent post surgical infection. See Rybak et al., *Vancomycin Therapeutic Guidelines: A Summary of Consensus Recommendations From The Infectious Diseases Society of America*, The American Society Of Health-System Pharmacists, and The Society Of Infectious Disease Pharmacists, CID 2009:49 (1 August), pg. 325.

Gentamicin is an aminoglycoside antibiotic used to treat many types of bacterial infections particularly those caused by susceptible Gram-negative bacteria. It has been used in a surgical setting because it acts against pathogens such as pseudomonas aeroginosa and escherichia coli. Gentamicin has been used in other surgical applications (e.g. compounded with bone cement in orthopedic settings). Gentamicin impregnated with biodegradable collagen implant (sponge) is currently being used in several markets outside of the US for the prevention of surgical site infections (SSI). However, two large pivotal phase III studies showed higher incidence of SSI in patients receiving the gentamicin sponge (colorectal surgery) and no difference in the incidence of SSI vs. standard of care (cardiothoracic surgeries). See generally, E. Bennett-Guerrero, NEJM, 2010, 1-10; and E. Bennett-Guerrero, JAMA, Aug. 18, 2010, 755-762.

Both vancomycin and gentamicin are very hydrophilic antibiotics. They are also both difficult to formulate into injectable depots based on phospholipids or other high oil phase content formulations, as they are not freely soluble in phospholipid or oil.

In addition, by conducting a series of stability tests, it has now been found that vancomycin and gentamicin degrade by different mechanisms. Vancomycin loses its stability through hydrolysis while gentamicin degrades due to oxidation or adduct formation. Thus, formulations containing either one of the actives are generally sensitive to these conditions. Moreover, both vancomycin and gentamicin are heat-sensitive and cannot be sterilized by using heat, such as autoclaving or gamma-radiation.

Accordingly, attempting to formulate a depot comprising vancomycin, gentamicin or both along with a phospholipid and oil provide many practical challenges. One such attribute includes the formulation should not feature high viscosity since the formulation has to be sterilized by filtering through a sterilizing membrane, such as one having pores of about 0.2 micron or less. There also remain certain dichotomous problems. For instance, these two particular actives have compatibility problems with phospholipids which, like viscosity, suggests a need to keep phospholipid content low. However, the need for coherent and cohesive gel formation and proper release characteristics suggest just the opposite.

Accordingly, there remains a long felt need for storage stable phospholipid depots containing vancomycin, gentamicin, a pharmaceutical salt thereof or a mixture thereof that can be administered by subcutaneous or intramuscular injection, by intraincisional injection or placement into surgical wound or other body tissues, vessels or cavities.

BRIEF SUMMARY OF THE INVENTION

One aspect of the present invention provides a process for making a depot comprising at least one hydrophilic water-soluble pharmaceutically active agent comprising: (1) mixing at least one hydrophilic water-soluble pharmaceutically active agent selected from the group consisting of vancomycin, gentamicin, a pharmaceutically acceptable salt thereof and a mixture thereof, water, a phospholipid, and an oil to form an oil-in-water "emulsion"; (2) homogenizing the emulsion to obtain a "primary emulsion"; (3) microfluidizing the primary emulsion to obtain a "monophasic solution," (4) ensuring that the pH of the primary emulsion and/or the monophasic solution is between about 3 to about 6, and in one embodiment, from about 3 to about 5, and in another embodiment, from about 3 to about 4 by adjusting the pH as necessary, (5) lyophilizing the monophasic solution of desired pH to obtain a dry paste, (6) adding a viscosity modifying agent to the dry paste in an amount sufficient to obtain a clear solution, (7) removing at least some of the viscosity modifying agent from the clear solution to obtain a depot having from about 5.5 wt % to about 7.5 wt % of the viscosity modifying agent relative to the total weight of the depot, and (8) sterilizing the depot by filtration.

In one embodiment, the steps of forming the emulsion and the primary emulsion can be combined as one step as long as the resulting product is the primary emulsion. In another embodiment, the steps of forming a primary emulsion and the monophasic solution can be combined as one step, as long as the resulting product is the monophasic solution. In yet another embodiment, the steps of forming the emulsion, the primary emulsion, and the monophasic solution can be combined as one step thereby going directly to the monophasic solution.

In an embodiment, the water present in the depot is no more than about 4 wt % relative to the total weight of the depot. In another embodiment, the water content of the depot is no more than about 2 wt %, and in still another embodiment, no more than about 1 wt %. In still a further embodiment, there is no more than about 0.5 wt % of water relative to the total weight of the depot. In other embodiments, the pharmaceutically active agents are vancomycin hydrochloride and gentamicin sulfate. In other embodiments, the depot is clear, and in yet other embodiments, the depot is ultra clear.

Another aspect of the present invention provides a process for making a clear depot comprising at least one hydrophilic water-soluble pharmaceutically active agent comprising: (1) dissolving at least one hydrophilic water-soluble pharmaceutically active agent selected from the group consisting of vancomycin, gentamicin, a pharmaceutically acceptable salt thereof and a mixture thereof in water to form an aqueous solution; (2) forming an oil-in-water emulsion comprising a phospholipid, an oil, and the aqueous solution comprising; (3) homogenizing the emulsion to obtain a primary emulsion; (4) microfluidizing the primary emulsion to obtain a monophasic solution, (5) adjusting the pH of the emulsion, primary emulsion and/or the monophasic solution to between about 3 to about 6, in another embodiment, from about 3 to about 5, and in yet another embodiment, from about 3 to about 4 as necessary, (6) lyophilizing the monophasic solution of desired pH to obtain a dry paste, (7) adding a viscosity modifying agent to the dry paste in an amount sufficient to obtain a desired viscosity and/or a desired clarity, (8) pre-filtering of the viscosity modified solution to obtain a clear solution, (9) removing at least some of the viscosity modifying agent from the clear solution to obtain a depot having from about 5.5 wt % to about 7.5 wt % of the viscosity modifying agent relative to the total weight of the depot, and (10) sterilizing the depot without substantial heating. Such sterilization procedures may be done by filtration among other methods. In another embodiment, pre-filtering and removing the viscosity modifying agent are optional steps. In one embodiment, the at least one hydrophilic water-soluble pharmaceutically active agent is vancomycin, gentamicin, a pharmaceutically acceptable salt thereof and a mixture thereof.

Yet another aspect of the present invention provides a method for making a depot comprising: (1) forming an oil-in-water emulsion including a phospholipid, an oil, at least one hydrophilic water-soluble pharmaceutically active agent selected from the group consisting of vancomycin, gentamicin, a pharmaceutically acceptable salt thereof or a mixture thereof and water; (2) converting the emulsion to a monophasic solution having a pH of between about 3 to about 6; (3) lyophilizing the monophasic solution to obtain a dry paste, (4) adding a viscosity modifying agent to the dry paste in an amount sufficient to obtain a viscosity modified solution, (5) removing at least some of the viscosity modifying agent to obtain a depot, and (6) sterilizing the depot, wherein the depot is clear.

In an embodiment, the method further comprises a step of aseptically filling the depot into a syringe, a vial or any other appropriate device capable of storing and/or delivering the depot to the treatment site or wound.

In accordance with another aspect of the invention, a stabilizing agent is optionally dissolved in water along with the pharmaceutically acceptable ingredient(s). In yet another aspect of the invention, a stabilizing agent is optionally mixed along with the pharmaceutically acceptable ingredient(s), water, a phospholipid, and an oil. Examples of the stabilizing agent includes, but are not limited to EDTA disodium, glycine, L-histidine, citric acid, mithionine, ascorbic acid, L-cysteine, alpha-tocopherol, and mixtures thereof. In yet another aspect of the invention, the depot does not include a stabilizing agent.

In an embodiment, in the step of forming the oil-in-water emulsion, the amount of water added is about 60 wt % to about 80 wt % relative to the total weight of the resulting emulsion. In another embodiment, the amount of water in the emulsion in the step of forming the oil-in-water emulsion is about two times the weight of the emulsion.

In yet another embodiment, after the step of microfluidizing the primary emulsion, which results in a monophasic solution, also referred to herein as "nanoemulsion", the nanoemulsion droplet size has an average diameter of less than about 120 nm, less than about 100 nm, or less than about 80 nm.

The reduction of average diameter of the droplet size of the nanoemulsion/monophasic solution is believed, without limitation, to reduce the viscosity of the resulting monophasic solution, allowing sterilization through a filter, rather than by using a heat-based sterilization system, such as by autoclaving or gamma-radiation sterilization, which can affect stability of vancomycin and/or gentamicin.

Before the step of microfluidization, the primary emulsion is generally a white, opaque, thick yogurt-like mass. After microfluidization, the resulting monophasic solution is generally clear, translucent, and water-like in viscosity and flow properties.

Although the present invention is not limited by any particular theory of operation, it is believed that very hydrophilic vancomycin, gentamicin, a pharmaceutically acceptable salt thereof or a mixture thereof, can be formulated with phospholipids to form a monophasic solution as defined herein resulting in storage stable depots with desirable properties. It is believed that the extremely small nanoemulsion droplets provided during microfluidization may be instrumental in the eventual properties of the depots produced, among other factors that may be involved.

In accordance with another embodiment of the present invention, the pH of the emulsion, primary emulsion and/or the monophasic solution is from about 3 to about 6, from about 3 to about 5, or from about 3 to about 4. And if not, the pH could be adjusted to that it fell in the desired range.

In accordance with yet another embodiment of the present invention, the pH of the depot, the final product, is from about 3 to about 6, from about 3 to about 5, and in another embodiment, from about 3 to about 4.

Another aspect of the present invention is a depot comprising at least one hydrophilic water-soluble pharmaceutically active agent selected from the group consisting of vancomycin, gentamicin, a pharmaceutically acceptable salt thereof and a mixture thereof, water, a phospholipid, and one or more of an oil, optionally a pH adjusting agent, and a viscosity modifying agent, wherein the water present in the depot is no more than about 4 wt %, no more than about 2 wt %, no more than about 1 wt %, or no more than about 0.5 wt % of water relative to the total weight of the depot. In another embodiment, the depot is syringeable.

In one embodiment of the present invention, the depot comprises both vancomycin and gentamicin. In another embodiment, the depot comprises pharmaceutical salts of one or both vancomycin and gentamicin. In another embodiment, the depot comprises either vancomycin or gentamicin. In yet another embodiment, the depot comprises a pharmaceutical salt of either vancomycin or gentamicin.

The depots in accordance with the present invention are, in one embodiment, "clear." This offers advantages in being able to see entrapped air, foreign bodies, and the like to prevent the unintended introduction of same into the body. Interestingly, it has also been discovered that when both vancomycin and gentamicin are present in the depot, the depot of the invention is clearer than when the depot contains either vancomycin or gentamicin alone. In such embodiment where both vancomycin and gentamicin are present in the depot, the clarity of such depot is "ultra clear" as defined herein. In an embodiment where the depot comprises either vancomycin or gentamicin, the clarity of such depot is "translucent" or "clear" as defined herein.

In one embodiment, the viscosity modifying agent is ethanol, wherein the amount of ethanol present in the depot is from about 3 wt % to about 25.0 wt %, about 4 wt % to about 10 wt %. In still another embodiment, the amount of ethanol present ranges from between about 5 wt % to about 6.5 wt % relative to the total weight of the depot. In yet another embodiment, the viscosity modifying agent is absolute ethanol.

In an embodiment, the viscosity modifying agent may be added to the dry paste until the amount of viscosity modifying agent is about 75 wt % or more of the viscosity modified solution. In other embodiments, the amount of viscosity modifying agent is about 50 wt % or more, and in still another embodiment, about 30 wt % or more. Finally, the amount of viscosity modifying agent is about 25 wt % or more relative to total weight of the viscosity modified solution.

In yet another embodiment, the amount of phospholipid present in the depot is from about 5 wt % to about 95 wt %, and in another embodiment, from about 25 wt % to about 75 wt % relative to the total weight of the depot. In another embodiment, the amount of phospholipids ranges from about 35 wt % to about 60 wt % relative to the total weight of the depot.

In accordance with another embodiment of the present invention, the amount of oil present in the depot is from about 5 wt % to about 95 wt %, and in another embodiment, from about 25 wt % to about 75 wt % relative to the total weight of the depot. In yet another embodiment, the amount of oil ranges from about 35 wt % to about 60 wt % relative to the total weight of the depot.

In accordance with an embodiment of the present invention, no more than about 80% of vancomycin and/or gentamicin are released at two hours when measured in accordance with a USP method I using 500 ml of deionized water as a medium. In another embodiment, no more than about 50%, and in yet another embodiment, no more than about 20% of vancomycin and/or gentamicin are released at two hours when measured in accordance with a USP method I using 500 ml of deionized water as a medium.

In accordance with another aspect of the invention, the depot optionally comprises a stabilizing agent to improve the stability of vancomycin, gentamicin or both. Examples of the stabilizing agent include, but not limited to EDTA (disodium edentate), glycine, L-histidine, citric acid, mithionine, ascorbic acid, L-cysteine, alpha-tocopherol, and mixtures thereof. In accordance with yet another aspect of the invention, the depot does not contain a stabilizing agent. In still another embodiment, the amount of stabilizing agent used, if any, will not negatively impact the stability of each active, vancomycin or gentamicin, in the depot.

In another aspect of the invention, a depot as described herein is provided in an applicator, syringe, vial or any other device capable of storing and/or delivering the depot to the treatment site, depot site or wound.

Another aspect of the present invention is a method of administering, via intradermal, intramuscular, intraincisional, subcutaneous, instillation or topically, the depot of the invention comprising a hydrophilic water-soluble pharmaceutically active agent selected from the group consisting of vancomycin, gentamicin, a pharmaceutically acceptable salt thereof or a mixture thereof, water, phospholipid, an oil, optionally a pH adjusting agent and a viscosity modifying agent to a patient in need thereof.

Yet another aspect of the present invention is a method of preventing and/or treating post surgical infection by introducing a depot of the present invention.

Another aspect of the present invention is a method of preventing and/or treating infection comprising administering a depot of the present invention which achieves sufficiently high local tissue concentrations sufficient to treat and/or prevent infections at a local site, without toxicity to kidney and/or other organs, and without contributing to the emergence of drug resistant strains of bacteria.

In another aspect, there is a method of rendering localized tissue unable to sustain pathogenic microorganisms by administering a depot of the present invention to the wound.

Yet another aspect of the present invention is a method of rendering localized tissue unable to sustain pathogenic microorganisms by administering a depot of the present invention without causing toxicity to kidney and other organs, and without causing emergence of drug resistant strains of bacteria.

BRIEF DESCRIPTION OF THE DRAWINGS

FIG. 14 illustrates the differential scanning calorimetry (DSC) analysis of Examples 10A and 10D

DETAILED DESCRIPTION

Figure 1:
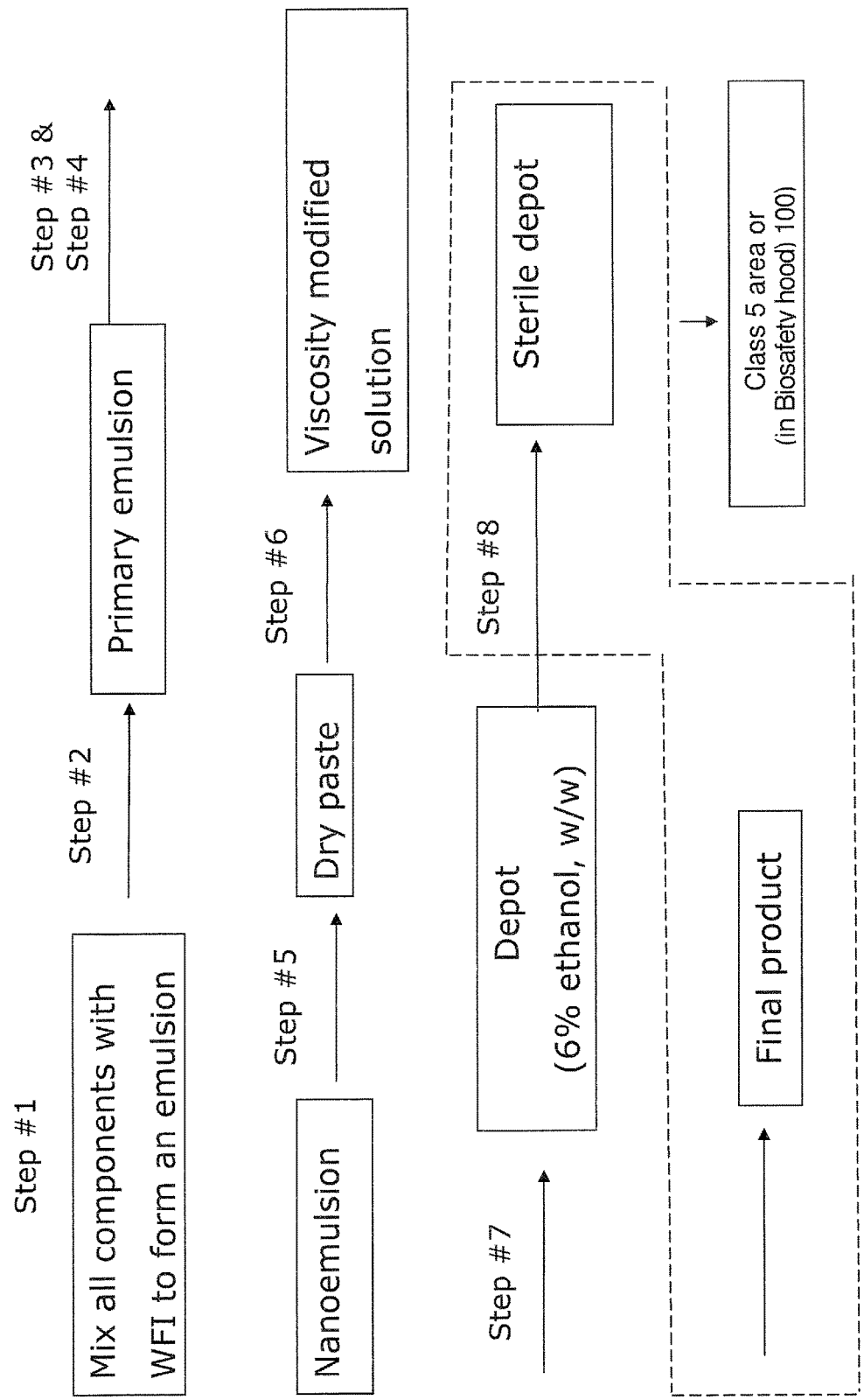
FIG. 1 is a process flow diagram of an embodiment of the method of making an inventive composition in accordance with an aspect of the invention.

The present invention will be described in more detail below.

While the specification concludes with the claims particularly pointing and distinctly claiming the invention, it is believed that the present invention will be better understood from the following description. All percentages and ratios used herein are by weight of the total composition and all measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

Note that while the specification and claims may refer to a final product such as, for example, a depot or other dosage form of the invention as, for example, containing a pH at an intermediate state, it may be difficult to tell from the final dosage form that the recitation is satisfied. However, such a recitation may be satisfied if the materials used prior to final production meet that recitation. Similarly, the amount of ingredients introduced into, for example, the emulsion, if described as being by weight may change relative to the weight of the product at some other phase of production such as, in the final depot, which may weight more or less. It is sufficient that those weight percentages were correct at any steps of production and/or in any intermediate. Indeed, as to any property or characteristic of a final product which cannot be ascertained from the dosage form directly, it is sufficient if that property resides in the components recited just prior to final production steps.

The term "emulsion" used herein is a system of two immiscible liquid phases. One of the two phases (the internal phase, discontinuous phase or discrete phase) is distributed as droplets/globules through the second phase (the external or continuous phase). As used herein, emulsions include oil-in-water (O/W) emulsions, in which a less polar liquid commonly referred to as an oil is in the internal phase; and water-in-oil (W/O) emulsions, in which an aqueous or other relatively polar liquid is in the internal phase.

The term "primary emulsion" used herein refers to a resulting product of the homogenization step, which may employ, for example, a high shear mixer.

The term "monophasic solution" and "nanoemulsion" are used interchangeably herein. It is noted that the term "solution" in "monophasic solution" does not mean that it is a homogeneous mixture of two or more substances, but that it is a resulting product of the microfluidization step, which may employ, for example, a high-pressure microfluidizer.

The term "monophasic," "one phase" and "one phase-like" are used to mean that the resulting product will remain as one phase without separation of phases or precipitation even after 6000 g centrifugation for 10 minutes at 25 deg C. in 1 g sample quantity, using a centrifuge made by Heraeus, Model Biofuge Fresco or any equivalent.

The term "viscous" as used here means that the viscosity of the composition is from about 1 centipoise to about 5000 centipoise, from about 200 centipoise to about 2000 centipoise, or from about 300 centipoise to about 1500 centipoise.

The term "syringeable" as used herein means that the composition may be administered with a syringe or a catheter or withdrawn from a vial into a syringe. It does not mean, however, that the composition of the invention must actually be in a syringe or administered using a syringe unless the specific recitation or the context suggests that meaning.

The term "translucent" and "clear" are used interchangeably herein to mean that the final depot or any of the intermediate step composition, such as a solution, emulsion, primary emulsion, nanoemulsion, and/or a gel, is not hazy or opaque, and that it is free from visually suspended particles. It should also be free of bubbles. Moreover, by translucent, it is meant that the depot and/or any of the intermediate composition, such as a solution, emulsion, primary emulsion, nanoemulsion, and/or a gel, is free from visually suspended particles and should also be free of bubbles. Moreover, by "translucent" or "clear," it is also meant that the depot and/or any of the intermediate composition, such as a solution, emulsion, primary emulsion, nanoemulsion, and/or a gel, of the present invention has a light transmittance of greater than about 90% measured at 800 nm (T800) in a 1 cm path quartz cuvette using alcohol as blank when measured by a UV-visible spectrophotometer, such as the one made by Pharmacia, Model Ultrospec III.

By "hazy" or "opaque," it is meant that a T800 value of the depot is less than about 90%.

By "ultra clear," it is meant that a T800 value of the depot is greater than about 92%, or 95%.

The term "stable" as used herein means that (1) the formulation remains clear at 25 deg C. for at least one year, or (2) the formulation remains clear and does not separate out or precipitate after centrifugation when the formulation is exposed to 40 deg C. for one week.

The term "gel" and "depot" are used interchangeably herein.

Process Description

As shown in FIG. 1, one aspect of the present invention provides a process for making a depot comprising a hydrophilic water-soluble pharmaceutically active agent selected from the group consisting of vancomycin, gentamicin, a pharmaceutically acceptable salt thereof, and a mixture thereof, comprising: (1) mixing at least one hydrophilic water-soluble pharmaceutically active agent selected from the group consisting of vancomycin, gentamicin, a pharmaceutically acceptable salt thereof and a mixture thereof, water, a phospholipid, and an oil to form oil-in-water emulsion (see FIG. 1, Step 1); (3) homogenizing the emulsion to obtain a primary emulsion (see FIG. 1, Step 2); (4) microfluidizing the primary emulsion to obtain a monophasic solution, also referred to herein and in FIG. 1 as a nanoemulsion (see FIG. 1, Step 3), (4) ensuring that the pH of the primary emulsion and/or the monophasic solution is between about 3 to about 6, a range of from about 3 to about 5, or a range of from about 3 to about 4 by adjusting the pH as necessary (see FIG. 1, Step 4), (5) lyophilizing the monophasic solution of desired pH to form a dry paste (see FIG. 1, Step 5), (6) adding a viscosity modifying agent to the dry paste in an amount sufficient to obtain a clear solution, (see FIG. 1, Step 6) (7) removing at least some of the viscosity modifying agent from the clear solution to obtain a depot having from about 5.5 wt % to about 7.5 wt % of the viscosity modifying agent relative to the total weight of the depot (see FIG. 1, Step 7), and (8) sterilizing the depot without heating the depot (see FIG. 1, Step 8).

In an embodiment of the present invention, the step of mixing at least one hydrophilic water-soluble pharmaceutically active agent selected from the group consisting of vancomycin, gentamicin, a pharmaceutically acceptable salt thereof and a mixture thereof, water, a phospholipid, and an oil to form an oil-in-water emulsion comprises (1) dissolving vancomycin, gentamicin, a pharmaceutically acceptable salt thereof and a mixture thereof in water to form an aqueous solution; and (2) forming an emulsion comprising a phospholipid, an oil, and an aqueous solution comprising the hydrophilic water-soluble pharmaceutically acceptable ingredient(s) selected from the group consisting of vancomycin, gentamicin, a pharmaceutically acceptable salt thereof or a mixture thereof.

In an alternate embodiment, a viscosity modifying agent is added to the dry paste in an amount sufficient to obtain a desired viscosity, and then the viscosity modified solution is pre-filtered to obtain a clear solution.

In one embodiment, the water present in the depot is no more than about 4 wt %, no more than about 2 wt %, no more than about 1 wt %, or no more than about 0.5 wt % of water relative to the total weight of the depot. In other embodiments, the pharmaceutically active agents are vancomycin hydrochloride and gentamicin sulfate. In other embodiment, the depot is clear, and in yet another embodiment, the depot is ultra clear.

Forming Oil-in-Water Emulsion

At least one hydrophilic water-soluble pharmaceutically active agent selected from the group consisting of vancomycin, gentamicin, a pharmaceutically acceptable salt thereof and a mixture thereof, water, a phospholipid, and an oil are mixed to form an oil-in-water emulsion.

In another embodiment, first, vancomycin hydrochloride, gentamicin sulfate or both are dissolved in water to form an aqueous solution.

The initial drug concentration of vancomycin hydrochloride in water is from about 1 mg/ml to about 50 mg/ml or from about 20 mg/ml to about 30 mg/ml, and initial drug concentration of gentamicin sulfate in water is from about 1 mg/ml to about 75 mg/ml, or from about 10 mg/ml to about 30 mg/ml.

Then the aqueous solution of vancomycin and/or gentamicin, phospholipid, oil, optionally a pH adjusting agent and optionally a stabilizing agent is mixed to form an oil-in-water emulsion.

Homogenizing to Obtain a Primary Emulsion

Subsequently, the emulsion may be homogenized using a high shear mixer (such as for example Silverson Model L5M mixer) to form a primary emulsion.

Microfluidizing to Obtain a Monophasic Solution

The primary emulsion was then microfluidized by using, for example, a high-pressure microfluidizer, to obtain a nanoemulsion/monophasic solution. The resulting nanoemulsion/monophasic solution has an average diameter of less than 120 nm, less than 100 nm, and or less than 80 nm to form a monophasic solution/nanoemulsion. It is found that the droplet size greater than 180 nm may result in a cloudy solution.

The reduction of average diameter of the nanoemulsion droplets is believed, without limitation, to reduce the viscosity of the resulting monophasic solution, allowing sterilization through a filter, rather than by using a heat-based sterilization system, such as by autoclaving or gamma-radiation sterilization, which can affect stability of vancomycin and/or gentamicin.

Before the step of microfluidization, the primary emulsion is generally a white, opaque, thick yogurt-like mass. After microfluidization, the resulting monophasic solution is generally clear, translucent, and water-like in viscosity and flow properties.

In order to produce a clear monophasic solution, the oil-in-water emulsion advantageously contains about 10% to about 80% water, from about 30% to about 80% water, or from about 60% to 80% water relative to the total weight of the oil-in-water emulsion in order to have the desired flow property to be processed in the high-pressure homogenizer, such as a MICROFLUIDIZER.

Adjusting pH

The pH of the emulsion, primary emulsion or monophasic solution may be adjusted by adding a pH adjusting agent so that the pH of the emulsion, primary emulsion or monophasic solution is from about 3 to about 6, a range of about 3 to about 5, or a range of from about 3 to about 4.

In another embodiment, this step is performed by adding an appropriate amount of a pH adjusting agent to the emulsion, followed by high shear mixing homogenization step for about 1 minute. Then, after the homogenization step, the pH of the composition is checked and may be adjusted again if necessary.

Lyophilization, Sublimation or Evaporation

By removing the water, gentamicin and/or vancomycin become uniformly dispersed in the phospholipid/oil vehicle. Water is then removed from the monophasic solution by lyophilization, sublimation and/or evaporation so that the amount of residual water in the resulting dry paste or the final syringeable clear depot is lower than about 4 wt %, lower than about 2 wt %, or lower than about 0.5 wt % of water relative to the total weight of the dry paste or viscous clear depot.

In another embodiment, the monophasic solution is freeze-dried using a tray lyophilizer. In yet another embodiment, the tray of the lyophilizer is stainless steel.

In yet another embodiment, the liquid filling height in the stainless steel lyophilization tray is no more than about 3 cm. In an embodiment, after the step of lyophilization, the resulting product, which is the dry paste, has no more than 1 wt % of water relative total weight of the dry paste.

Addition of Viscosity Modifying Agent

The viscosity modifying agent is added to the dry paste until the dry paste is completely dissolved. The viscosity modifying agent may be added to the dry paste until the amount of viscosity modifying agent is about 75 wt % or more, about 50 wt % or more, about 30 wt % or more or about 25 wt % or more relative to total weight of the viscosity modified solution. In one embodiment, the viscosity modifying agent and the dry paste may be mixed at a temperature of about 10 deg C. to about 80 deg C., or about 25 deg C. to about 60 deg C.

Pre-Filtration

This is an optional step and is not required for certain embodiments of the invention. If the viscosity modified solution obtained after adding the viscosity modifying agent is hazy, the viscosity modified solution may be filtered using for example 0.65 micron filter to form a clear solution. The hazy component removed by the pre-filtration steps consists of a small fraction of vancomycin (about 2% target assay) and gentamicin (3-4% target assay). This loss may be compensated by adjusting up the initial load or dropping the assay targets. This is an optional step and is not required for certain embodiments of the invention.

Removal of Viscosity Modifying Agent

Subsequently, the viscosity modifying agent which was added to dissolve the dry paste is removed. Removal of the viscosity modifying agent may be done until the amount of residual viscosity modifying agent which may be present in the depot from about 1% to about 50%, from about 2% to about 18%, or from about 5% to about 6.5% relative to the total weight of the depot.

If over-dried, the viscosity modifying agent may be added back as needed. Removal of the viscosity modifying agent may be done using a rotary evaporator or by blowing with nitrogen gas or air. Thermal gravimetric Analysis (TGA) can be used to measure the amount of viscosity modifying agent removed from the clear solution to form a depot.

The viscosity of the resulting depot in accordance with the present invention is from about 100 centipoise to about 5000 centipoise, from about 200 centipoise to about 2000 centipoise, or from about 300 centipoise to about 1500 centipoise. Viscosity measurement can be performed using any conventional method, including using a Brookfield Digital Programmable Rheometer with Model No. DV-III with Spindle No. SP-40. This is an optional step and is not required for certain embodiments of the invention.

Sterile Filtration

The depot is then sterilized by filtering through a sterilizing membrane, such as one having pores of about 0.2 micron or less.

Depot

Another aspect of the present invention provides a depot comprising at least one hydrophilic water-soluble pharmaceutically active agent selected from the group consisting of vancomycin, gentamicin, a pharmaceutically acceptable salt thereof and a mixture thereof, water, a phospholipid, an oil, a pH adjusting agent, and a viscosity modifying agent, wherein the water present in the depot is no more than about 4 wt %, no more than about 2 wt %, or no more than about 0.5 wt % of water relative to the total weight of the depot.

In accordance with another aspect of the invention, the depot optionally comprises a stabilizing agent to improve the stability of vancomycin, gentamicin or both. In another aspect of the invention, this depot is provided in a syringe, vial or any other device capable of delivering the depot to the treatment site, depot site or wound.

Pharmaceutical Active Ingredient

The pharmaceutical active ingredient in accordance with the present invention is vancomycin, gentamicin, a pharmaceutically acceptable salt thereof or a mixture thereof. In one embodiment, the pharmaceutical active ingredient in accordance with the present invention is vancomycin hydrochloride, gentamicin sulfate or a mixture thereof. In another embodiment, the pharmaceutical active ingredients in accordance with the present invention are vancomycin hydrochloride and gentamicin sulfate. In yet another embodiment, the pharmaceutical active ingredient in accordance with the present invention is either vancomycin hydrochloride or gentamicin sulfate.

Examples of the pharmaceutically acceptable salt include, but not limited to, any acids that can form salts with either vancomycin or gentamicin such as acetic acid, hydrochloric acid, hydrobromic acid, citric acid, formic acid, lactic acid, succinic acid, sulfuric acid, and the like.

The amount of the pharmaceutical active ingredients that may be present in the depot can vary with a number of parameters including the size of the total intended dose, the duration of administration, the size of the depot and where and how it will be administered, the type of active to be administered, the pattern of administration (e.g., continuous, delayed, etc.) and the like. However, generally, the total amount of the pharmaceutically acceptable ingredient may be from about 0.001 wt % to about 20 wt %, from about 0.01 wt % to about 10 wt %, or from about 0.1 wt % to about 5 wt % relative to the total weight of the depot.

Oil

An oil in accordance with the present invention may be, for instance, natural oils such as vegetable oils, animal oil, vitamin E, vitamin E ester, and the like and/or synthetic or semisynthetic oils, or mixtures thereof.

A vegetable oil refers to oil derived from plant seeds or nuts. Examples of vegetable oils include, but are not limited to, almond oil, borage oil, black currant seed oil, castor oil, safflower oil, soybean oil, sesame oil, cottonseed oil, grapeseed oil, sunflower oil, canola oil, coconut oil, palm oil, orange oil, corn oil, olive oil and the like.

An animal oil refers to triglyceride oil derived from an animal source. Examples of animal oil can be fish oil, or from other sources such as tallow, lard and the like.

Examples of synthetic or semisynthetic oils are mono-, di- or triglycerides, whose acid components are C6 to C20 saturated and/or unsaturated fatty acids, CAPTEX® (various grades of propylene glycol esters such as propylene glycol didecanoate, and glycerol esters such as glyceryl tricaprylate/caprate); MIGLYOL® (caprylic/capric acid triglycerides; or caprylic/capric/linoleic acid triglycerides; or caprylic/capric/succinic acid triglycerides; or propylene glycol diester of caprylic/capric acid and admixtures with other agents; CAPMUL® (available in different grades, e.g. Capmul MCM. It is mainly mono- and di-esters of glycerol and of propylene glycol, such as glyceryl mono-oleate and propylene glycol monocaprylate. Another grade consists of polyethylene glycol glyceryl monostearate. In one embodiment, the oil used in accordance with the present invention is sesame oil.

The amount of the oil that may be present in the depot may be from about 5 wt % to about 95 wt %, from about 25 wt % to about 75 wt %, or from about 35% to about 60% relative to the total weight of the depot.

In certain embodiments, the oil to phospholipid ratio in the depot may be within a range of from about 20:1 to about 1:20, from about 3:1 to about 1:3, or from about 1:2 to about 1:1, by weight.

Phospholipid

Phospholipid in accordance with the present invention refers to a lipid molecule containing one or more phosphate groups, including those derived from either glycerol (phosphoglycerides, glycerophospholipids) or sphingosine (sphingolipids).

In some embodiments, phospholipids are triglyceride derivatives in which one fatty acid has been replaced by a phosphate group and one of several nitrogen-containing molecules. The fatty acid chains are hydrophobic and the charges on the phosphate and amino groups make that portion of the molecule hydrophilic. The result is an amphiphilic molecule.

According to the United States Pharmacopoeia (USP), lecithin is a non-proprietary name describing a complex mixture of acetone-insoluble phospholipids, which comprise mainly of phosphotidylcholine, phosphotidylethanolamine, phosphotidylserine and phosphotidylinositol, combined with various amounts of other substances such as triglycerides, fatty acids and carbohydrates. The composition of lecithin and hence its physical properties vary depending upon the source of the lecithin and phospholipid composition, e.g., phosphotidylcholine content, etc.

In accordance with an embodiment of the present invention, lecithin used herein are pharmaceutical grade lecithins derived from egg or soybean, which have been used in parenteral products and are substantially free from irritating, allergenic, inflammatory agents or agents that cause other adverse biological reactions.

In accordance with the practice of the present invention, the selection of phospholipid for preparing the depot is determined based on the ability of the phospholipid to (1) be chemically compatible with the at least one hydrophilic water-soluble pharmaceutically active agent selected from the group consisting of vancomycin, gentamicin and a mixture thereof, (2) form a monophasic solution and maintain the small droplet size through the manufacturing process and during storage, and (3) provide the desired depot and provide the desired release of the pharmaceutically active agent.

Examples of the phospholipid include, but not limited to, sphingolipids in the form of sphingosine and derivatives (obtained from soybean, egg, brain and milk), gangliosides, and phytosphingosine and derivatives (obtained from yeast).

Phospholipids can also be synthesized and examples of common synthetic phospholipids include, but not limited to, diglycerols, such as 1,2-dilauroyl-sn-glycerol (DLG), 1,2-dimyristoyl-sn-glycerol (DMG), 1,2-dipalmitoyl-sn-glycerol (DPG), 1,2-distearoyl-sn-glycerol (DSG); phosphatidic acids, such as 1,2-dimyristoyl-sn-glycero-3-phosphatidic acid, sodium salt (DMPA, Na), 1,2-dipalmitoyl-sn-glycero-3-phosphatidic acid, sodium salt (DPPA, Na), 1,2-distearoyl-sn-glycero-3-phosphatidic acid, sodium salt (DSPA, Na); phosphocholines, such as 1,2-didecanoyl-sn-glycero-3-phosphocholine (DDPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1,2-dilinoleoyl-sn-glycero-3-phosphocholine (DLOPC), 1,2-dierucoyl-sn-glycero-3-phosphocholine (DEPC), 1,2-dieicosapentaenoyl-sn-glycero-3-phosphocholine (EPA-PC), 1,2-didocosahexaenyl-sn-glycero-3-phosphocholine (DHA-PC), 1-myristoyl-2-palmitoyl-sn-glycero-3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-palmitoy-sn-glycero-3-phosphocholine (SPPC), 1-myristoyl-2-oleoyl-sn-glycero-3-phosphocholine (MOPC), 1-palmitoyl-2-oleoy-sn-glycero-3-phosphocholine (POPC), 1-stearoyl-2-oleoyl-sn-glycero-3-phosphocholine (POPC); phosphoethanolamines, such as hydrogenated soybean phosphoethanolamine (HSPE), non-hydrogenated egg phosphoethanolamine (EPE), 1,2-dilauroyl-sn-glycero-3-phosphoethanolamin (DLPE); 1,2-dimyristoyl-sn-glycero-3-phosphoethanolamin (DMPE); 1,2-dipalmitoyl-sn-glycero-3-phosphoethanolamin (DPPE); 1,2-distearoyl-sn-glycero-3-phosphoethanolamin (DSPE); 1,2-dioleoyl-sn-glycero-3-phosphoethanolamin (DOPE); 1,2-dilinoleoyl-sn-glycero-3-phosphoethanolamin (DLoPE); 1,2-dierucyl-sn-glycero-3-phosphoethanolamin (DEPE), 1,2-palmitoyl-sn-glycero-3-phosphoethanolamin (POPE); phosphoglycerols such as hydrogenated soy bean phosphatidylglycerol, sodium salt (HSPG, Na), non-hydrogenated egg phosphatidylglycerol, sodium salt (EPG, Na), 1,2-dilauroyl-sn-glycero-3-phosphoglycerol, sodium salt (DLPG, Na), 1,2-dimyristoyl-sn-glycero-3-phosphoglycerol, sodium salt (DMPG, Na), 1,2-dimyristoyl-sn-glycero-3-phospho-sn-1-glycerol, ammonium salt (DMP-sn-1-G, NH$_4$), 1,2-dipalmitoyl-sn-glycero-3-phosphoglycerol, sodium salt (DPPG, Na), 1,2-distearoyl-sn-glycero-3-phosphoglycerol, sodium salt (DSPG, Na), 1,2-distearoyl-sn-glycero-3-phospho-sn-1-glycerol, sodium salt (DSP-sn-1G, Na), 1,2-dioleoyl-sn-glycero-3-phosphoglycerol, sodium salt (DOPG, Na), 1,2-dierucyl-sn-glycero-3-phosphoglycerol, sodium salt (DEPG, Na), 1,2-palmitoyl-sn-glycero-3-phosphoglycerol, sodium salt (POPG, Na); phosphotidylserines such as 1,2-dimyristoyl-sn-glycero-3-phospho-L-sine, sodium salt (DMPS, Na), 1,2-dipalmitoyl-sn-glycero-3-phospho-L-sine, sodium salt (DPPS, Na), 1,2-distearyl-sn-glycero-3-phospho-L-sine, sodium salt (DSPS, Na), 1,2-dioleoyl-sn-glycero-3-phospho-L-sine, sodium salt (DOPS, Na), 1-palmitoyl-2-oleoyl-sn-glycero-3-phospho-L-sine, sodium salt (POPS, Na); mixed chain phospholipids, such as 1-palmitoyl-2-oleoyl-sn-glycero-3-phosphocholine (POPC), 1-palmitoyl-2-oleoyl-sn-glycero-3-phospoglycerol, sodium salt (POPG, Na), 1-palmitoyl-2-oleoyl-sn-glycero-3-phosphoglycerol, ammonium salt (POPG, $NH_4$): lysophospholipids, such as 1-myristoyl-2-lyso-sn-glycero-3-phosphocholine (S-lyso-PC), 1-palmitoyl-2-lyso-sn-glycero-3-phosphocholine (P-lyso-PC), 1-stearoyl-2-lyso-sn-glycero-3-phosphocholine (S-lyso-PC); and pegylated phospholipids, such as N-(carbonyl-methoxypolyethyleneglycol 2000)-MPEG-2000-DPPE, 1,2-dipalmitoyl-sn-glycero-3-phosphoethanolamine, sodium salt, N-(carbonyl-methoxypolyethyleneglycol 5000)-MPEG-5000-DSPE, 1-2-distearoyl-sn-glycero-3-phosphoethanolamine, sodium salt, N-(Carbonyl-methoxypolyethyleneglycol 5000)-MPEG-5000-DPPE, 1,2-dipalmitoyl-sn-glycero-3-phosphoethanolamine, sodium salt, N-(carbonyl-methoxypolyethyleneglycol 750)-MPEG-750-DSPE, 1,2-distearoyl-sn-glycero-3-phosphoethanolamine, sodium salt, N-(carbonyl-methoxypolyethyleneglycol 2000)-MPEG-2000-DSPE, 1,2-distearoyl-sn-glycero-3-phosphoethanolamine, sodium salt.

The amount of the phospholipids that may be present in the depot can vary with a number of parameters including the viscosity of final formulation, the duration of administration, the size of the depot and where and how it will be administered, the type of active to be administered, the pattern of administration (e.g., continuous, delayed, etc.) and the like. However, generally, the amount of the phospholipid that may be present in the depot may be from about 5% to about 95% relative to the total weight of the composition, or about 35% to about 60% relative to the total weight of the composition.

Water

Water which can be used in accordance with the present invention includes, but not limited to distilled and deionized water, or any other aqueous liquid which is capable of dissolving the hydrophilic water-soluble vancomycin and/or gentamicin and capable of subliming/evaporating during the lyophilization step.

In order to obtain a monophasic solution, for example, by using a high pressure microfluidizer, the oil-in-water emulsion may contain from about 50% to about 90% water, from about 60% to about 80% water, or from about 70% to about 80% water relative to the total weight of the oil-in-water emulsion in order to have the desired flow property to be processed in the homogenizer, such as a MICROFLUIDIZER.

However, once the monophasic solution is obtained, most of water may be removed by for example, lyophilization, sublimation and/or evaporation.

Vancomycin degrades due to hydrolysis, and the amount of residual water in the final depot affects the long term stability of vancomycin. When vancomycin precipitates, the depot turns from translucent to hazy or separates into two phases as shown in EXAMPLE 3 herein.

Accordingly, in accordance with the present invention, the amount of residual water must be maintained lower than about 4 wt %, lower than about 2 wt % or lower than about 0.5 wt % of water relative to the total weight of the viscous clear depot in order to maintain the vancomycin stable during storage.

pH Adjusting Agent

The pH adjusting agent in accordance with the present invention is any non-toxic acid, base or salt. Examples of pH adjusting agents include, but not limited to, hydrochloric acid, acetic acid, sulfuric acid, sodium hydroxide, potassium hydroxide, ammonium hydroxide, lysine, arginine, and the like.

As mentioned above, gentamicin degrades due to oxidation or adduct formation. As shown in EXAMPLE 4 hereinbelow, pH affects the long term stability of gentamicin, and when gentamicin precipitates, the depot turns from translucent to hazy.

Accordingly, pH of the depot may be from about 3 to about 6, a range of from about 3 to about 5, or a range of from about 3 to about 4.

Stabilizing Agent

A stabilizing agent in accordance with the present invention is a material which reduces catalytic effect of metal ion on the oxidation, hydrolysis or other degradation reactions and or increases stability of the hydrophilic water-soluble pharmaceutically active agent. Examples of such stabilizing agent include, but not limited to, EDTA (disodium edentate), glycine, L-histidine, citric acid, methionine, ascorbic acid, L-cysteine, alpha-tocopherol, and mixtures thereof. In certain embodiments, the amount of the stabilizing agent present in the depot is from about 0.001% to about 5.0% relative to the total weight of the composition, or about 0.01% to about 1.0% relative to the total weight of the composition. In another embodiment, the depot does not contain a stabilizing agent.

Viscosity Modifying Agent

A viscosity modifying agent in accordance with the present invention is an aqueous or non-aqueous (other than having a contaminant level of water) liquid which is capable of dissolving the dry paste formed after lyophilization, sublimation and/or evaporation.

Examples of a viscosity modifying agent include, without limitation, ethanol, isopropanol, and a mixture thereof. In one embodiment, the viscosity modifying agent is substantially non-aqueous. In another embodiment, the viscosity modifying agent is ethanol.

The viscosity modifying agent is added to the dry paste until the dry paste is completely dissolved in the agent. The resulting viscosity modified solution may also become "hazy." In one embodiment, the viscosity modifying agent and the dry paste are mixed at a temperature of about 10 deg C. to about 80 deg C., or in a range of about 50 deg C. to about 70 deg C., or in a range of about 25 deg C. to about 60 deg C.

The viscosity modifying agent is added to the dry paste until the amount of viscosity modifying agent is about 10 wt %, 20 wt %, 25 wt % or 30 wt % relative to total weight of the resulting solution. The resulting viscosity of the solution can be from about 10 to about 200 centipoise, from about 15 to about 100 centipoise, or about 20 centipoise to about 50 centipoise.

Viscosity can be determined using a Brookfield digital programmable rheometer with the SP-40 spindle or any other equivalent rheometer. More specifically, the starting RPM of the rheometer can be from 0.1 to 1.0, then reducing the RPM to 0.1 in 0.1 RMP increment every 30 seconds. The viscosity measurement can be recorded at 0.8 RMP at an ambient temperature of about 30 deg C.

Subsequently, some amount of the viscosity modifying agent used to dissolve the dry paste may be removed. The removal of the viscosity modifying agent may be done until the residual amount of viscosity modifying agent which may be present in the depot is from about 1 wt % to about 20 wt %, from about 2 wt % to about 18 wt %, or from about 5 wt % to about 6.5 wt % relative to the total weight of the depot. If over-dried, the viscosity modifying agent may be added back as needed.

The viscosity of the resulting depot in accordance with the present invention is from about 100 centipoise to about 5000 centipoise, from about 200 centipoise to about 2000 centipoise, or from about 300 centipoise to about 1500 centipoise.

Method of Treatment

Another aspect of the present invention is a method of administering via intradermal, intramuscular, intraincisional, subcutaneous, instillation or topically a depot of the present invention comprising vancomycin, gentamicin, a pharmaceutically acceptable salt thereof or a mixture thereof, water, phospholipid, an oil, optionally a pH adjusting agent and a viscosity modifying agent. The depot can be dosed at the desirable site using various dosages and at various dosing intervals depending upon the need. That is the depot should be sufficient to release the pharmaceutically active agent for a period of about at least one day with a dosing volume from about 0.1 mL to about 100 mL. For example, dosing intervals of once-a-day, once-every-other-day, once-every-3-days, once-a-week or once-a-month with a dosing volume from about 0.1 mL to about 100 mL can be used. Typically, the depot may be used in a single application and is generally instilled at the wound site before suturing the wound site.

Another aspect of the present invention is a method of preventing and/or treating infection including, without limitation, surgical site infection, comprising administering a depot of the present invention which achieves sufficiently high tissue concentration to treat and/or prevent infections at a local site, yet does not cause toxicity to kidney and/or other organs, and also does not cause and/or contribute to the emergence of drug resistant strains of bacteria.

In another aspect, there is provided a method of rendering localized tissue unable to sustain pathogenic microorganisms by administering a depot of the present invention to the wound.

In another embodiment, this is accomplished without causing toxicity to kidney and/or other organs, and without causing and/or contributing to the emergence of drug resistant strains of bacteria.

In each of the foregoing methods, the dose of vancomycin, gentamicin or both should be such that, when released from the depot, the localized tissue is unable to sustain pathogenic bacteria for at least 24 hours and, in another embodiment, at least 48 hours. In still another embodiment, the localized tissue is unable to sustain pathogenic bacteria for at least 3 days, for at least one week or for a period of one month.

Figure 10:
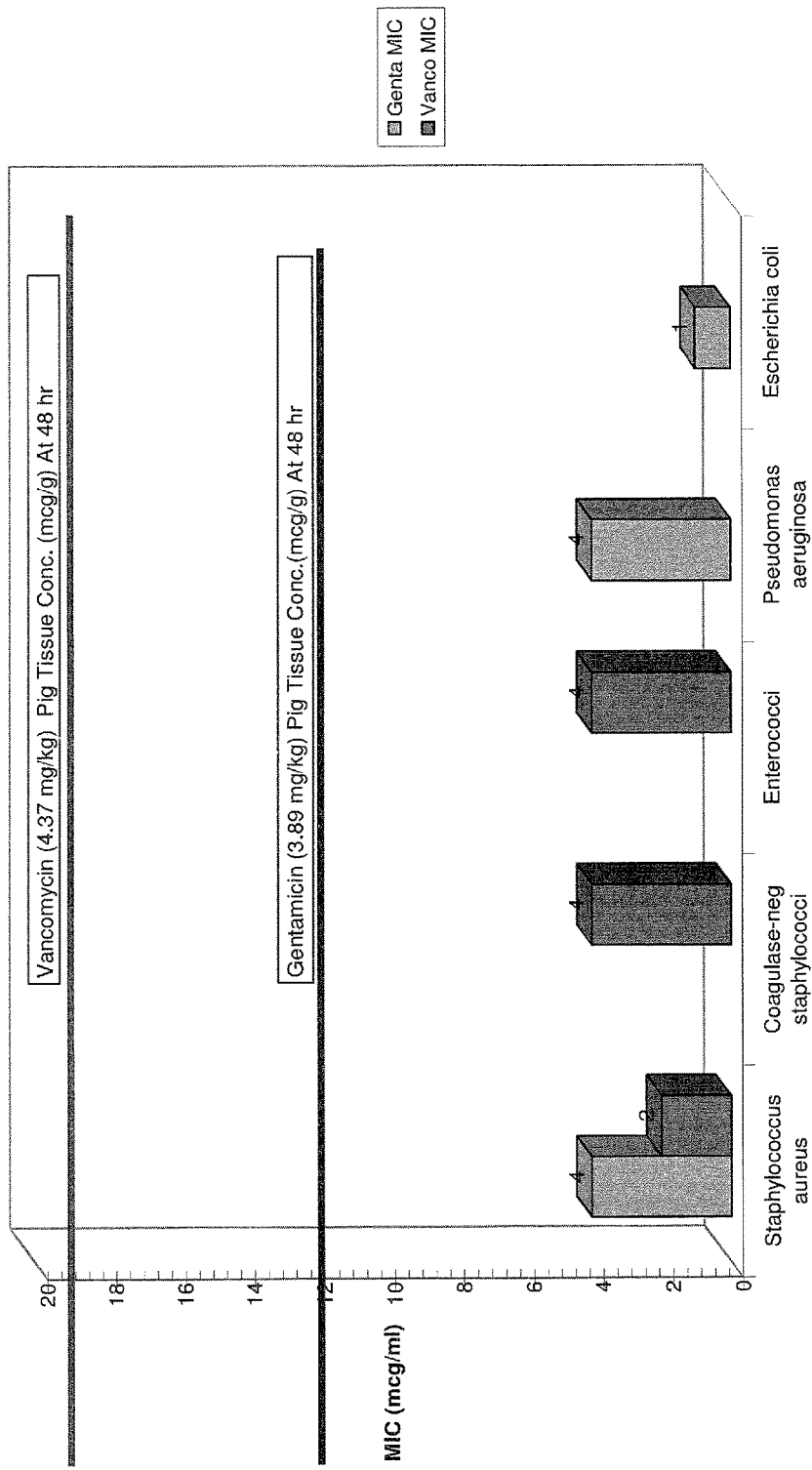
FIG. 10 illustrates tissue concentration in a pig when administered intraincisionally with a depot of the present invention vs. MIC 90 for top surgical site infection (SSI) pathogens

As shown in FIG. 10, and according to published data, the minimum inhibitory concentration required to inhibit the growth of 90% of the organisms ($MIC_{90\ (mcg/ml)}$) for well known surgical site infection (SSI) pathogens, such as staphylococcus aureus, coagulase-negative staphylococci, enterococci, pseudomonas aeruginosa, and Escherichia coli, are in the range of 1-4 mcg/ml. See generally, M. J. Rybak, et al., Vancomycin Therapeutic Guidelines, CID 2009:49 (1 August), 325-327; and A. I. Hidron, et al., Infection and Hospital Epidemiology, November 2008, vol. 29, No. 11, 996-1011. These are based on use of vancomycin and gentamicin individually as illustrated. When the depot of the present invention comprising vancomycin (4.37 mg/kg) and gentamicin (3.89 mg/kg) was administered to a pig, the localized pig tissue concentration of vancomycin achieved by the depot of the present invention was over 19 mcg/ml at 48 hrs, which is scientifically higher than the MIC 90 for the above-identified SSI pathogens. Similarly, the pig tissue concentration of gentamicin achieved by administering the depot of the present invention was about 12 mcg/ml at 48 hrs.

To this end, it is noted that the inventors did not inoculate pigs with the above-identified SSI pathogens and then administer the depot to the local site to determine the efficacy of the present invention. Nevertheless, the published MIC 90 data for the above-identified SSI pathogens, and the achievable tissue concentration of the formulation of the present invention comprising vancomycin and gentamicin demonstrate that the use of the depot of the present invention would be highly effective in providing localized drug levels effective for treating and/or preventing infection by rendering the localized tissue unable to sustain pathogenic microorganisms.

Figure 11:
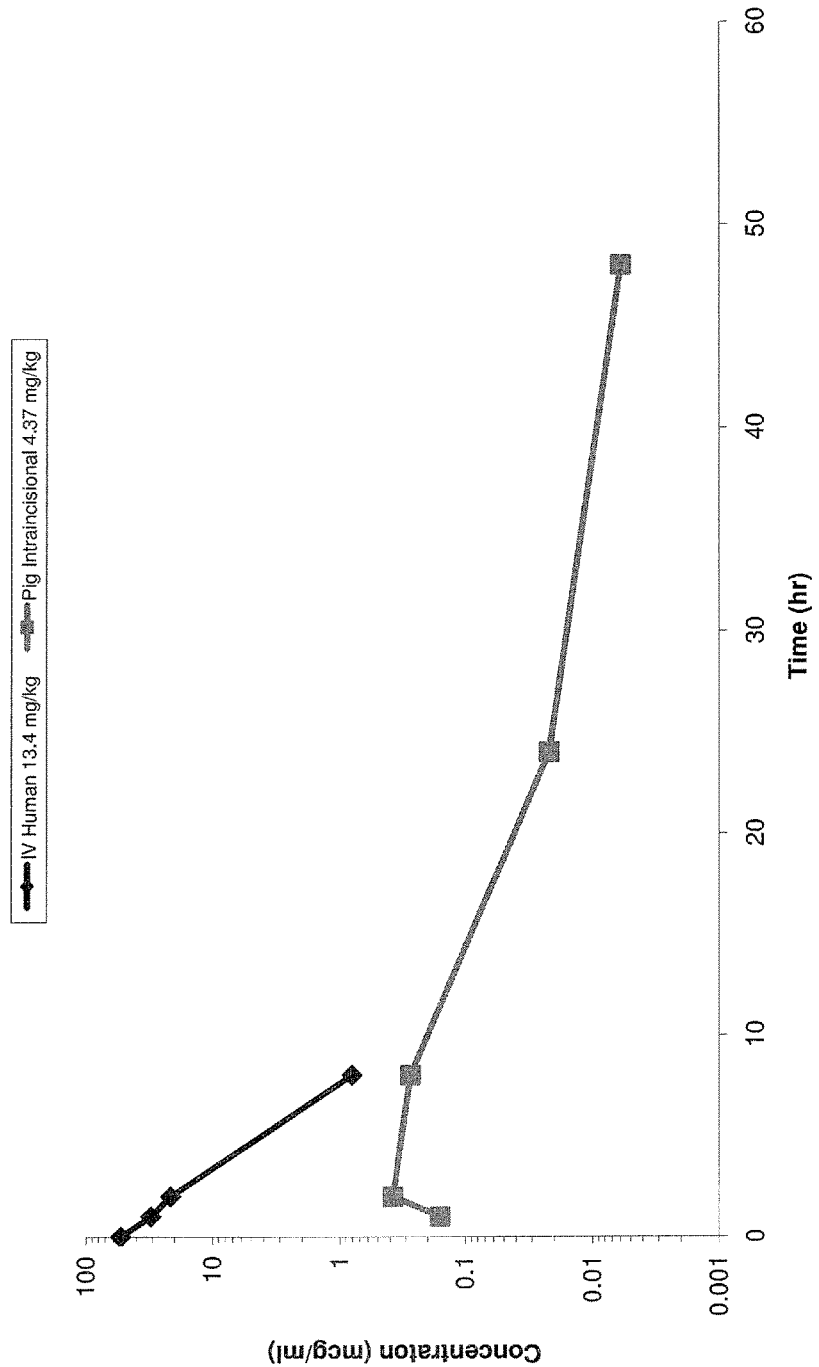
FIG. 11 illustrates comparison of vancomycin plasma concentration after therapeutic IV dose in humans vs. intraincisional administration of a formulation in accordance with the present invention in the pig.

FIG. 11 illustrates that the depots of the present invention when administered intraincisional to pigs provides high local tissue concentrations of both actives, vancomycin and gentamicin, and low systemic concentrations (plasma). The low systemic concentrations of gentamicin observed using the depot of the present invention provides a significant safety margin since gentamicin toxicity (renal and ototoxicity) are known to be related to plasma concentrations greater than 10 mg/L. See generally, D. S. Reeves, Infection 8 (1980) Suppl. 3, S 313-S320.

Vancomycin renal toxicity is also related to excessive drug exposure but cannot as easily be correlated to a specific peak concentration. However, the low systemic concentrations observed using the depot administration of the present invention have shown no systemic toxicity in the pig model for either drug and clearly are well below published values for gentamicin.

A second concern with vancomycin is the development of bacterial resistance. Vancomycin resistance can develop when the target tissues or ancillary tissues that colonize bacteria are exposed to sub-effective concentrations of vancomycin for significant periods of time. After systemic administration of vancomycin alone, the desired minimum plasma concentrations at steady-state are at least 10 mg/L or maybe in the range of about 15-20 mg/L. Given the low uptake of vancomycin by tissues from blood, these concentrations are sufficient to push therapeutically effective concentrations into the tissues and achieve a therapeutic effect. Blood concentrations serve as a surrogate marker for the target tissues wherein the goal is to achieve a plasma $AUC_{0-t}/MIC_{90}$ ratio of from about 400 to about 300,000 or $AUC_{0-t}/MIC_{90}$ ratio of $>400$ or $AUC_{0-t}/MIC_{90}$ ratio of $>1600$. This ratio is achieved when trough levels are maintained at the levels noted above.

With the depot of the present invention, very low concentrations of vancomycin are observed in circulating plasma while supra-therapeutic concentrations are present in the incision site where the gel was administered as shown in FIG. 10. Given the low level of uptake of vancomycin from plasma to tissue, the low systemic concentrations of vancomycin lead to negligible levels of vancomycin in tissues distal from the incision site. The only mechanism for transport is via the plasma and the amount of uptake by the tissues from the plasma is low. Therefore, the probability of vancomycin resistance developing at sites distal from the incision should be very low.

Thus in another aspect of this invention there is provided a method of treating a patient comprising administering to said patient a therapeutically effective dose of vancomycin alone or in combination with gentamicin or pharmaceutically acceptable salts thereof such that a plasma $AUC_{0-t}/MIC_{90}$ ratio of $>400$ is achieved for vancomycin so as to prevent emergence of resistance in s. aureus. In yet another aspect of this invention a patient receiving the above noted administration exhibits $1/10^{th}$ the steady-state trough serum concentration so as to avoid any nephrotoxicity exhibited by high dose administration of vancomycin by conventional methods. See generally, M. J. Rybak, Vancomycin Therapeutic Guidelines, CID 2009:49 (1 August), 325-327.

EXAMPLES

Example 1: Depot in Accordance with the Present Invention

TABLE 1

List Of Ingredients Of The Depot In Accordance With The Present Invention

| Component | w/w % |
|---|---|
| Gentamicin sulfate | Equivalent to 0.36% in the "USP Gentamicin Assay" value |
| Vancomycin hydrochloride | Equivalent to 0.24% in the "USP Vancomycin Assay" value |
| Soy lecithin (Phospholipon 90G or PL90G) | 53.3 |
| L-Histidine | 0.1 |
| Ethanol | 6.0 |
| Sesame oil | 40.0 |
| TOTAL | 100% |

First, a 500 mL beaker was charged with 0.36 g gentamicin sulfate, 0.24 g vancomycin hydrochloride, 53.3 g PL90G, 40 g sesame oil and 0.1 g L-histidine. To this was then added Water for Injection (WFI) and the mixture was homogenized by a high shear mixer at 5000 RPM for 15 min. The resulting monophasic solution was lyophilized to remove water to obtain a dry paste with less than 0.2% residual moisture.

Example 2: Effect of Water Content on Appearance of Example 1

This dry paste was mixed with water and/or ethanol, to form a viscosity modified solution and used in several of the studies, including EXAMPLE 2 to EXAMPLE 5 as set forth hereinbelow.

Various amounts of water (from 1.1 wt % to 4.1 wt %) and ethanol (at 6 wt %) were added into the dry paste of EXAMPLE 1 to produce several samples. Samples were mixed well by a BeadBeater mixer, centrifuged to remove air bubble, and then observed for initial appearance ("Initial sample"). Also, samples were passed thru 0.45 µm filter and the filtrates were stored at 2-8° C. for further appearance observation ("Filtered sample"). Table 2 shows the effect of water content on the appearance of the formulations. It was found that water content significantly affected the appearance of the formulations:

TABLE 2

Effect Of Water Content On The Appearance Of Example 1 Formulations

| Sample ID | S-1 | S-2 | S-3 | S-4 | S-5 | S-6 | S-7 | S-8 |
|---|---|---|---|---|---|---|---|---|
| Water (%) | 1.14 | 1.46 | 1.83 | 2.05 | 2.61 | 3.06 | 3.70 | 4.07 |
| Initial sample | | Hazy | | | | Clear | | 2 phases |

TABLE 2-continued

Effect Of Water Content On The Appearance Of Example 1 Formulations

| Sample ID | S-1 | S-2 | S-3 | S-4 | S-5 | S-6 | S-7 | S-8 |
|---|---|---|---|---|---|---|---|---|
| Filtered sample | All clear after filtration. However, with more water, a delayed precipitation occurred at 2-8° C. after about 3 to 7 days. | | | | | | | Not tested |

Example 3: Effect of Water Content on Gentamicin and Vancomycin Stability

The effect of residual water content on gentamicin and vancomycin stability of the formulations of EXAMPLE 1 was evaluated by a 60 min autoclave treatment. As summarized in Table 3 below, it was found that vancomycin had reduced stability in terms of recovery or purity at the higher residual water level. No significant effect of water on gentamicin stability was observed in the same range.

TABLE 3

Effect Of Water Content On Gentamicin And Vancomycin Stability

| | | Vancomycin | | Gentamicin |
|---|---|---|---|---|
| ID | | Recovery (% over Pre-autoclave) | Purity (%) | Recovery (% over Pre-autoclave) |
| EXAMPLE 1* (0.76% H$_2$O) | Pre-autoclave | 69.4 | 89.2 | 67.7 |
| | Autoclave | | 68.8 | |
| EXAMPLE 1* (1.26% H$_2$O) | Pre-autoclave | 65.7 | 89.9 | 80.2 |
| | Autoclave | | 64.5 | |
| Example 1* (1.76% H$_2$O) | Pre-autoclave | 62.0 | 89.5 | / |
| | Autoclave | | 63.2 | |
| Example 1* (2.26% H$_2$O) | Pre-autoclave | 60.5 | 88.8 | 77.5 |
| | Autoclave | | 58.8 | |
| | Autoclave | | 69.4 | |

*pH 5.7

Example 4: pH-Stability and pH-Solubility Profiles of Gentamicin and Vancomycin in Example 1 Formulation The pH adjusted formulations of EXAMPLE 1 were placed at 2-8 deg C. for appearance examination. (See Table 4 below.)

TABLE 4

Effect of pH on Appearance of EXAMPLE 1 Formulations

| | | Appearance | |
|---|---|---|---|
| pH | Water (%) | Before filtration | Filtrate at 2-8° C. |
| 3.21 | 0.17 | Clear | Clear |
| 5.54 | 0.15 | Hazy | Clear for 5-7 days, then hazy |
| 5.63 | 0.13 | | |
| 6.02 | 0.04 | | |
| 6.01 | 0.11 | | |
| 6.99 | 0.11 | | |
| 7.67 | 0.09 | | |

A pH-stability profile was generated by heating the samples from EXAMPLE 1 with a 60 minute autoclave treatment. (See Table 5 below.)

TABLE 5

Effect of pH on Stability of EXAMPLE 1 formulations

| | | Assay Recovery | | Vancomycin Purity (%) | |
|---|---|---|---|---|---|
| | | (% over the pre-treatment) | | Pre- | Post- |
| pH | Water (%) | Vancomycin | Gentamicin | treatment | treatment |
| 3.21 | 0.17 | 82.9 | 94.1 | 91.6 | 79.4 |
| 5.54 | 0.15 | 82.3 | 79.6 | 91.5 | 81.6 |
| 5.63 | 0.13 | 78.0 | 81.6 | 90.4 | 73.6 |
| 6.02 | 0.04 | 77.0 | 79.6 | 90.5 | 74.3 |
| 6.01 | 0.11 | 80.1 | 82.7 | 89.6 | 75.0 |
| 6.99 | 0.11 | 80.5 | 73.1 | 90.7 | 76.2 |
| 7.67 | 0.09 | 77.4 | 75.3 | 91.2 | 77.1 |
| 5.99 | 0.201 | 80.8 | 84.3 | 87.8 | 71.5 |

The results indicated that:

(1) pH affected EXAMPLE 1 formulations' appearance. The formulation was clear at pH 3.2;

(2) pH affected gentamicin's stability in the formulation. A low pH (e.g., from pH of 3 to 4) is preferred for gentamicin stability; and (3) pH did not affect vancomycin stability significantly.

Example 5: pH Stability Profile of Gentamicin in Example 1 Formulation Between pH of 3.0 to 5.5

Samples of EXAMPLE 1 formulation at three different pH levels between 3.0 to 5.5 were prepared. In addition, the effect of L-histidine on the stability of the formulation of EXAMPLE 1 was also tested comparing the formulation containing L-histidine with those that do not contain L-histidine. The stability of gentamicin and vancomycin was evaluated in the same way as set forth in EXAMPLE 3. It was found that (1) Stability of gentamicin in the formulation is pH-dependant (gentamicin preferred a low pH (e.g., from pH of 3 to 4));

(2) Stability of vancomycin in the formulation is less pH-sensitive in the pH range studied;

(3) L-histidine increased gentamicin stability in the pH range studied; and (4) L-histidine decreased vancomycin stability in the pH range studied.

Figure 2:
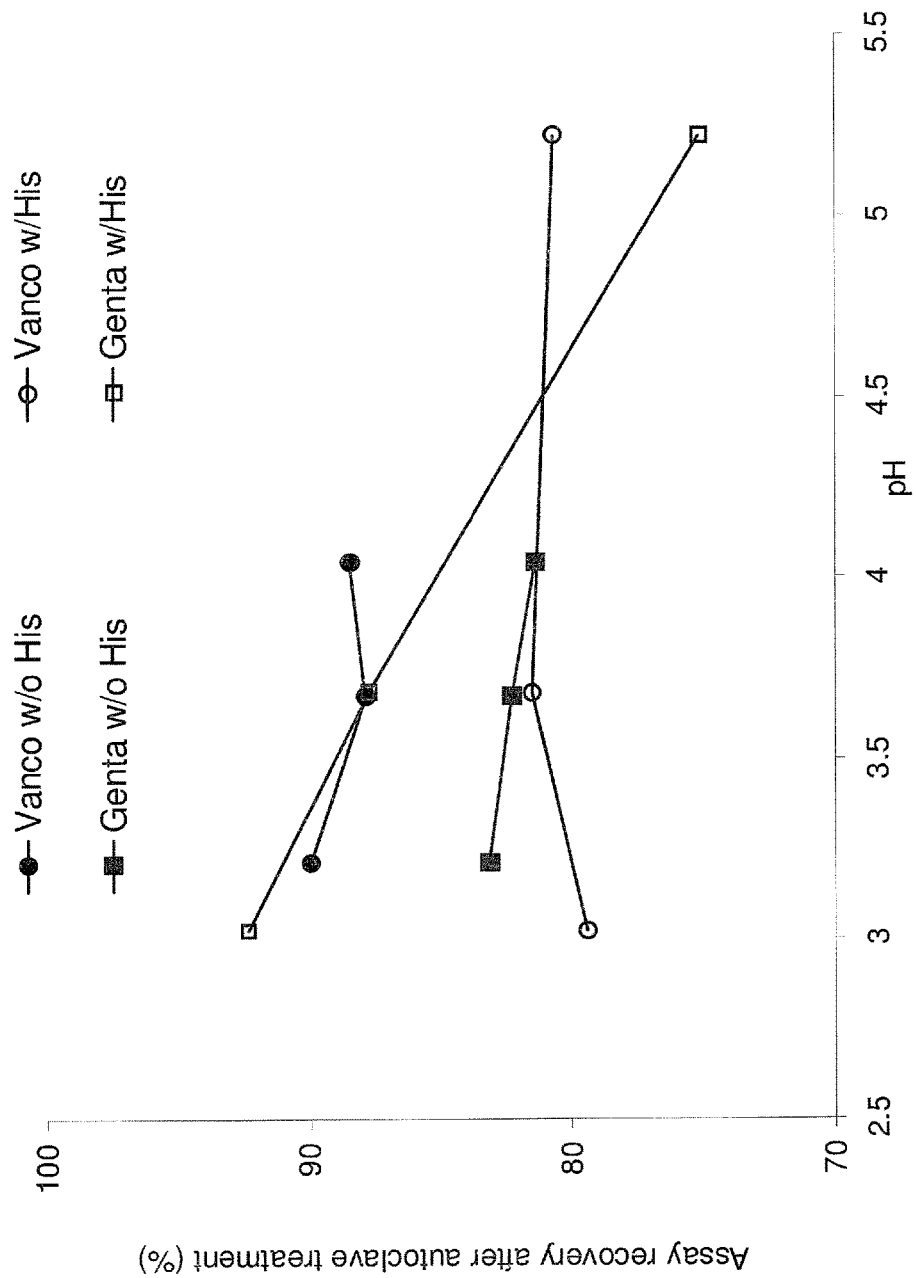
FIG. 2 shows the assay recovery of vancomycin and gentamicin of the formulation of EXAMPLE 1 after the autoclave treatment.

FIG. 2 shows the assay recovery after the autoclave treatment.

Example 6: Another Depot in Accordance with the Present Invention and the Process of Making the Formulation

TABLE 6

List Of Ingredients Of Another Depot In Accordance With The Present Invention

| Component | w/w % |
|---|---|
| Gentamicin sulfate | Equivalent to 1.675% in the "USP Gentamicin Assay" value |
| Vancomycin hydrochloride | Equivalent to 1.876% in the "USP Vancomycin Assay" value |
| Soy lecithin (PL90G) | 50.0 |
| Ethanol | 6.0 |
| Sesame oil | Qs to 100 |
| HCl | Enough to adjust to pH of 3.3 +/− 0.2 |

A clear yellow sterile depot (batch size: 1500 g), which contained less than 0.5 wt % of residual water having a pH of 3.3 was prepared by a multi-step process following the steps of: (1) emulsification, (2) homogenization/microfluidization, (3) lyophilization, (4) ethanol dilution, (5) pre-filtration, (6) ethanol removal and (7) filtration. Simple mixing of all of the ingredients listed above does not form a clear depot.

Detailed procedures for each of the above noted steps are as follows: First, water was added to gentamicin sulfate, vancomycin hydrochloride, to allow complete dissolution of gentamicin sulfate and vancomycin hydrochloride. Then, PHOSPHOLIPON® 90G (from Phospholipid GmbH) and sesame oil was added, followed by high shear mixing at 5000 rpm for 60 minutes to obtain a uniform primary emulsion. Then the pH of the primary emulsion was adjusted to 3.3±0.2 by adding 1N of HCl. This was done by adding an appropriate amount of 1N HCl to the emulsion, followed by high shear mixing for 1 minute. Then, the measurement of pH was taken to ensure that the primary emulsion had a pH of 3.3±0.2.

Subsequently, the primary emulsion was placed in a microfluidizer to produce a monophasic solution. The average diameter of the droplets of the monophasic solution was measured using a laser light scattering device.

Then, the monophasic solution was lyophilized to remove water to obtain a dry paste with less than 0.5% residual water. Then the dry paste was mixed with dehydrated alcohol. The mixture was then sonicated in a 60-70 deg C. water bath until a clear solution (viscosity modified) was obtained. Then the solution was cooled to room temperature, and was pre-filtered through a 0.65 micron sterile filter.

Then the alcohol from the solution was removed by blowing nitrogen gas until the residual amount of dehydrated alcohol was 6.5 wt %-7 wt % to obtain a viscous and clear gel. Dehydrated alcohol was added back as needed, if it was over dried.

In a biosafety hood, argon gas at 40 psi was applied to filter the depot through a 0.2 micron filter to sterilize the formulation. Then, in a biosafety hood, filtered depot was filled into a glass vial.

Example 7: In Vitro Release Profile

Figure 3:
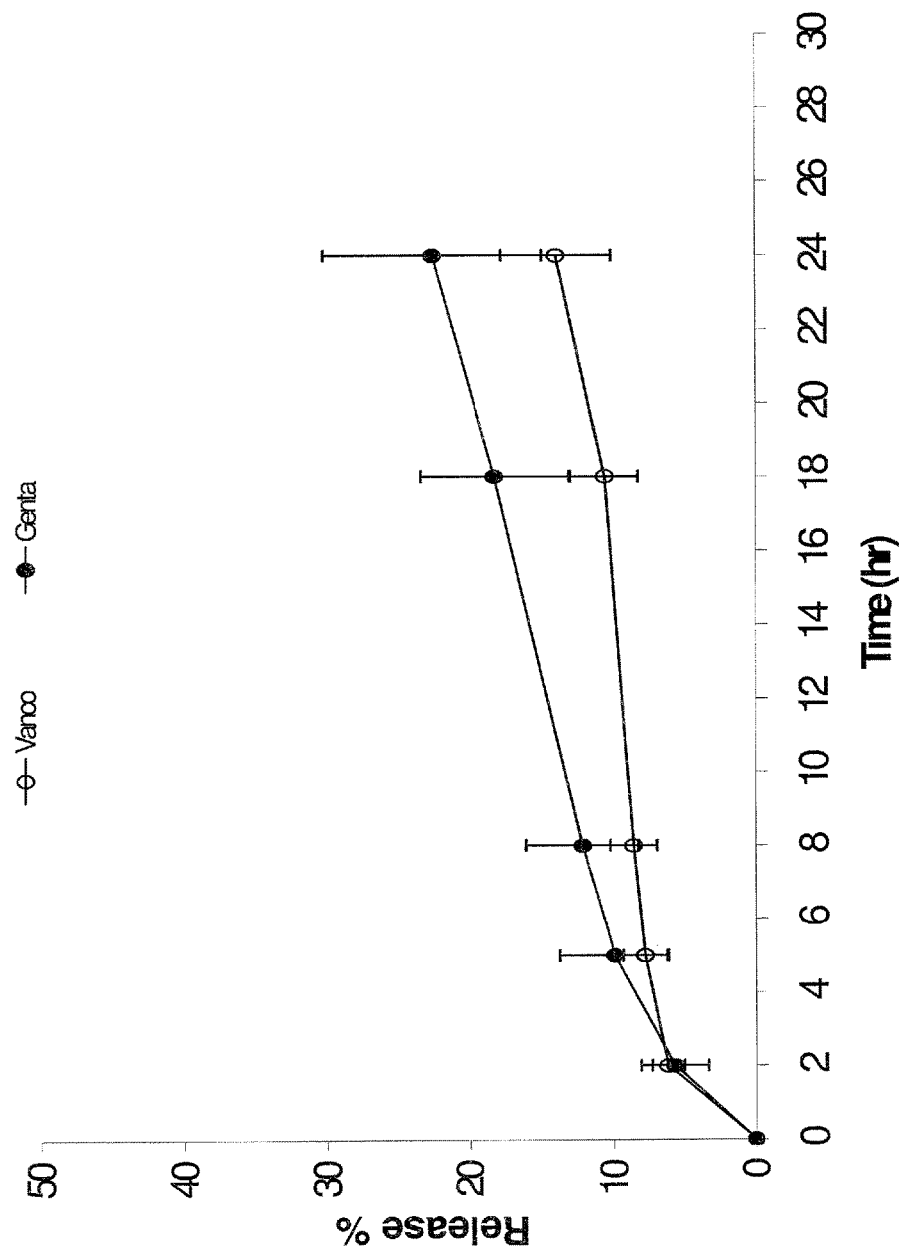
FIG. 3 is an in vitro release profile of gentamicin and vancomycin of the formulation of EXAMPLE 6 using USP method I.

In Vitro Release Profile of the Formulation of EXAMPLE 6 containing gentamicin and vancomycin was measured using the USP method I using basket apparatus (100 rpm at 37 deg C.). 1.36 g of EXAMPLE 6's formulation was filled in a 000 size capsule and the filled capsule was placed in 40 mesh basket with baffles. FIG. 3 shows an in vitro release profile of gentamicin and vancomycin of the formulation of EXAMPLE 6 using USP method I.

Figure 4:
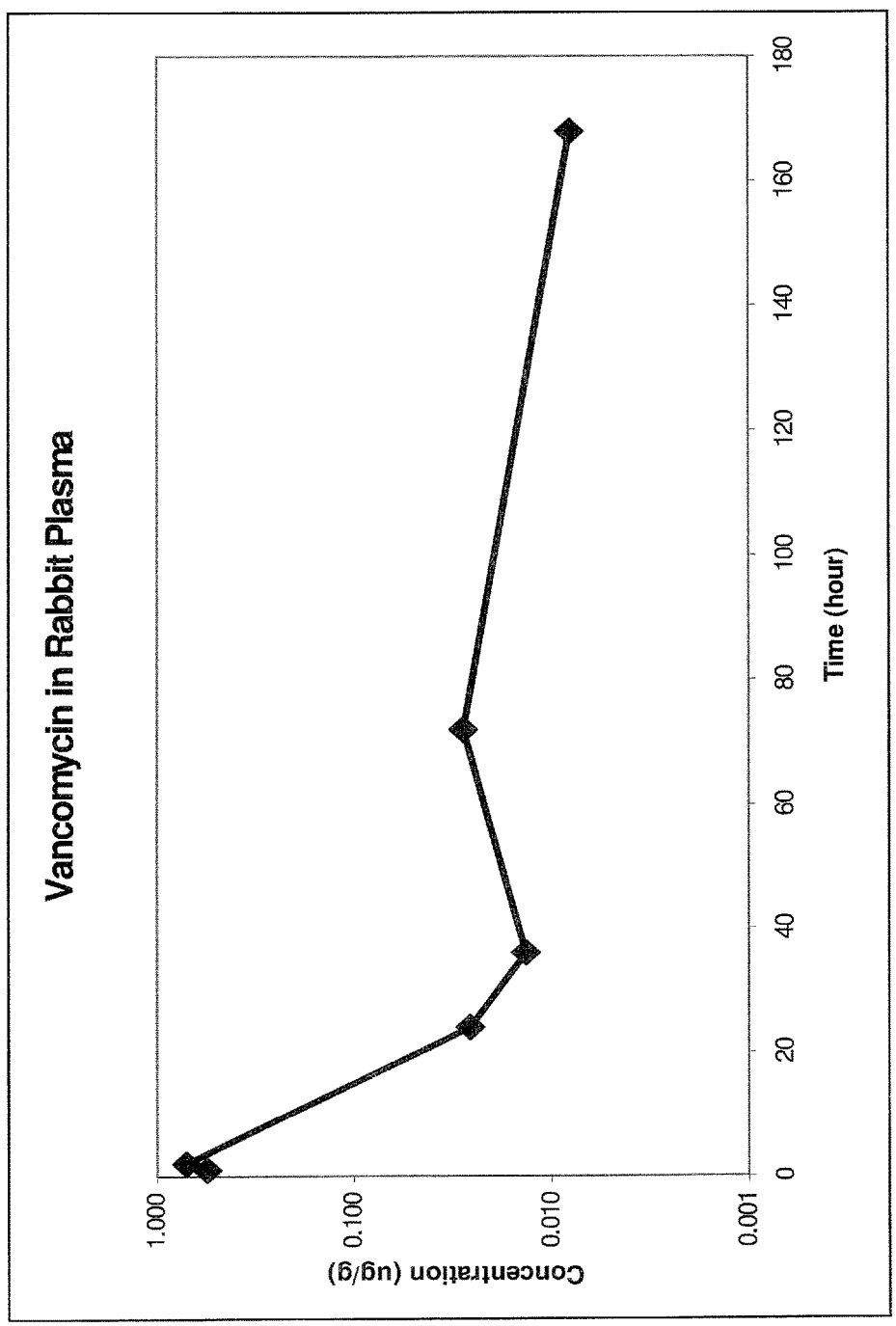
FIG. 4 illustrates plasma concentrations of vancomycin of the formulation of EXAMPLE 1 in rabbits.
Figure 5:
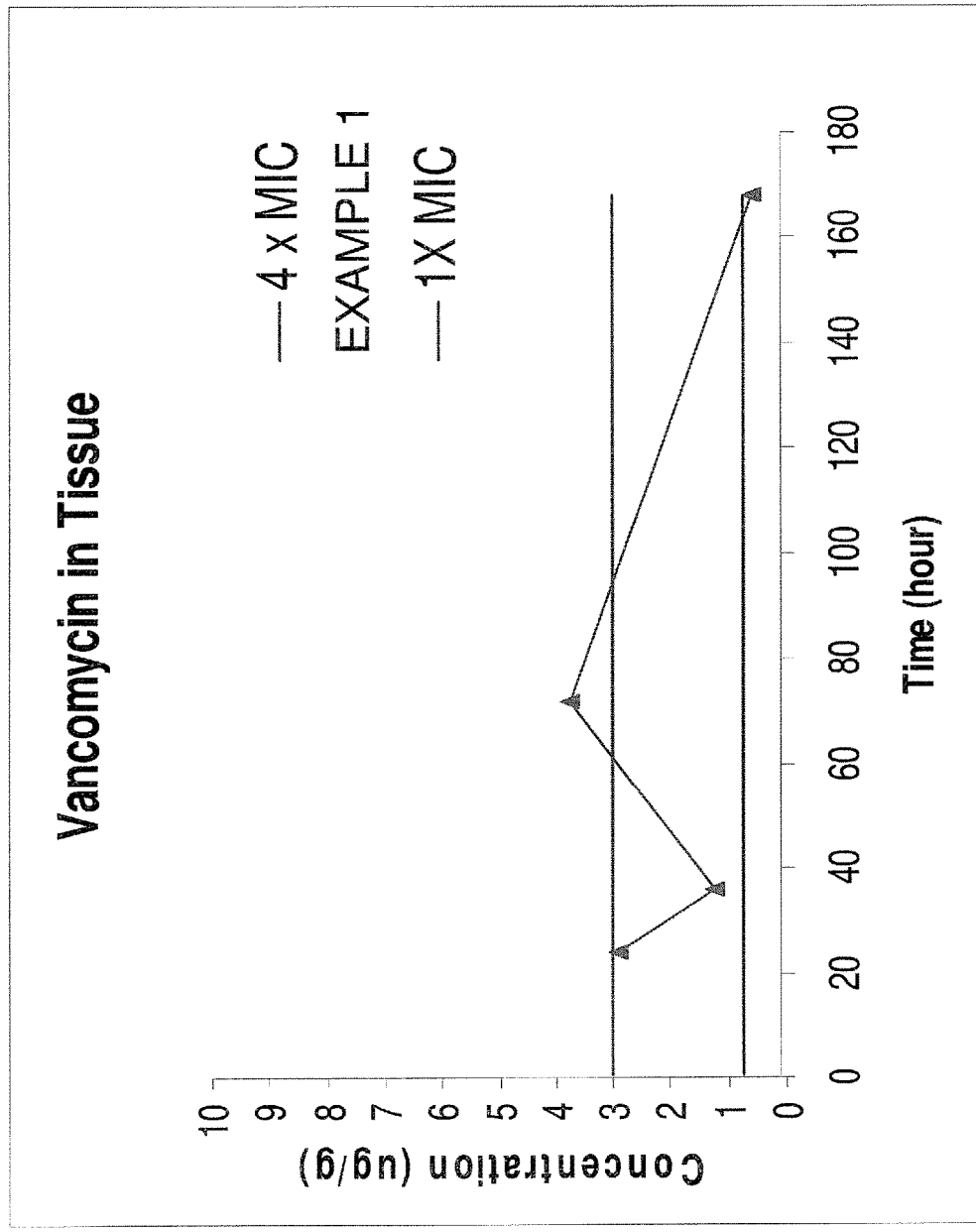
FIG. 5 illustrates tissue concentrations of vancomycin of the formulation of EXAMPLE 1 in rabbits.

EXAMPLE 1, vancomycin (Vanco) and gentamicin (Genta) were rapidly absorbed, with a plasma Tmax of 1-2 hours. Plasma Cmax concentrations were similar to those observed in the mouse. Plasma concentrations decreased to near the limit to quantification by 36 hours. Tissue concentrations of vancomycin peaked at 72 hours and were above the Minimum Inhibitory Concentration (MIC) through 168 hours, as shown in FIGS. 4 and 5.

Figure 6:
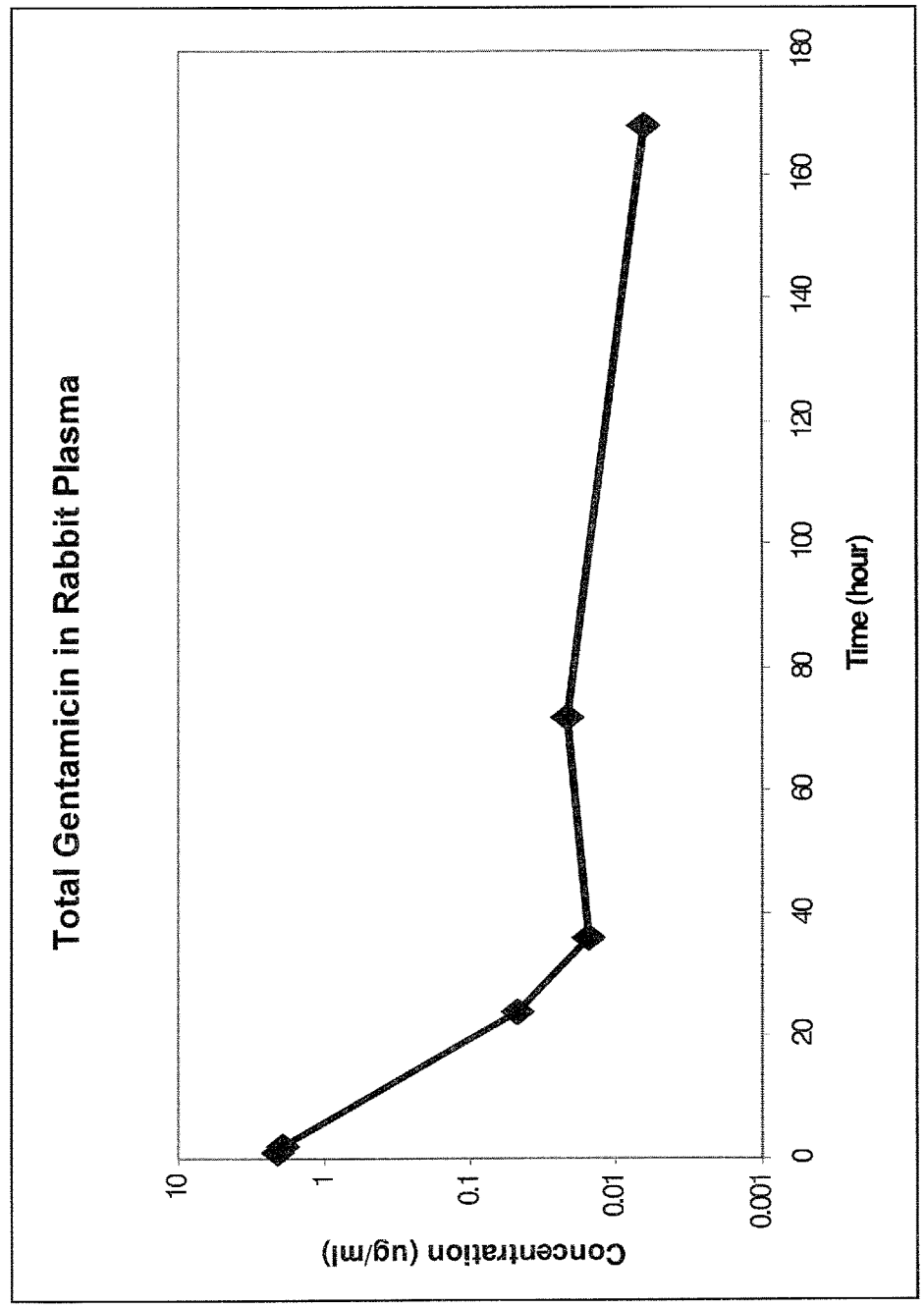
FIG. 6 illustrates plasma concentrations of gentamicin of the formulation of EXAMPLE 1 in rabbits.
Figure 7:
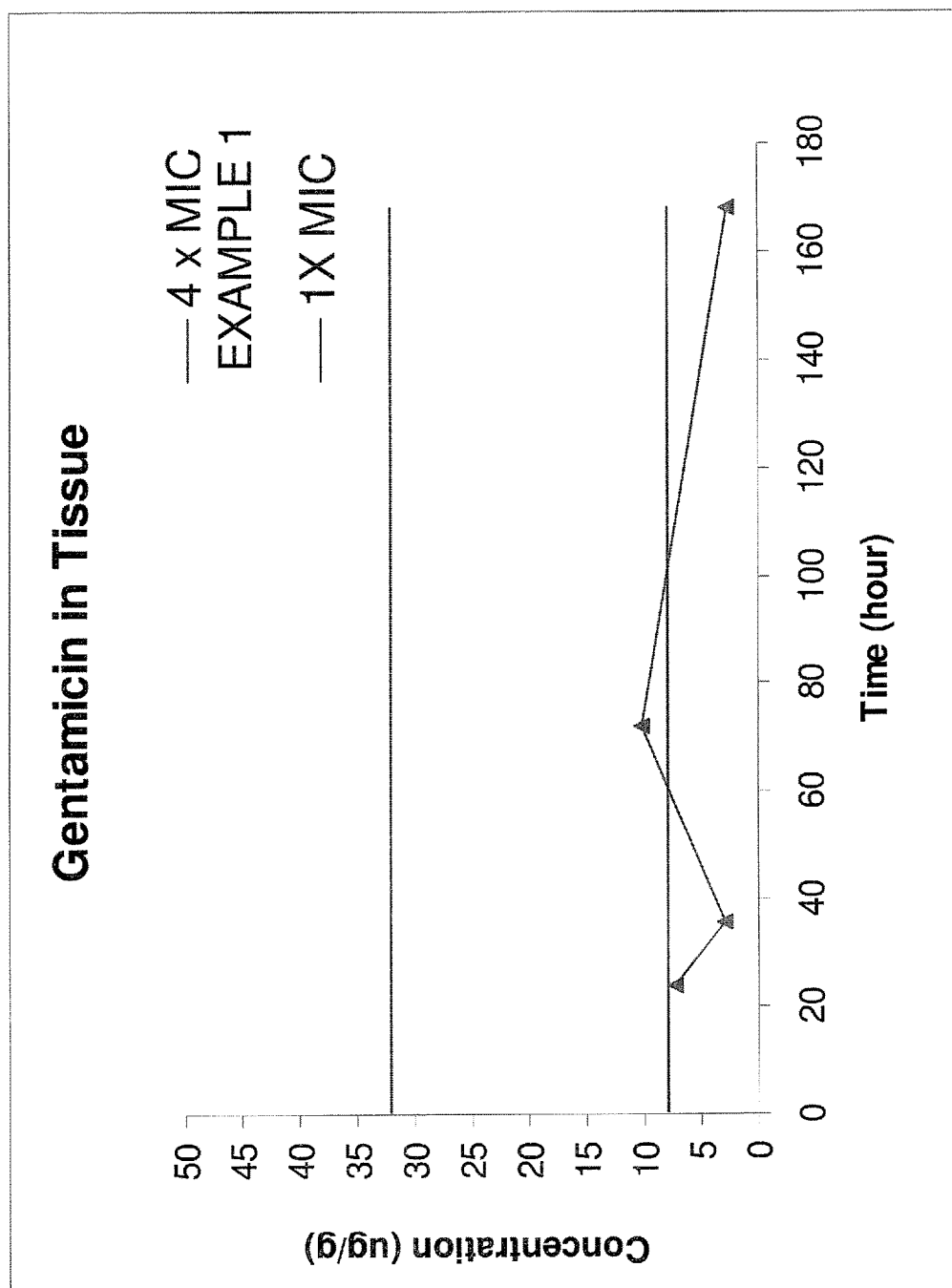
FIG. 7 illustrates tissue concentrations of gentamicin of the formulation of EXAMPLE 1 in rabbits.

Tissue concentrations of gentamicin peaked at 72 hours and were at or below the MIC through 168 hours, as shown in FIGS. 6 and 7.

Plasma and tissue analysis was performed by Liquid Chromatography/Mass spectrometry (LC-MS/MS) analysis and the Pharmacokinetic (PK) results of the formulation of EXAMPLE 1 are summarized in Tables 8 and 9, respectively below:

TABLE 8

Rabbit Plasma PK Parameters Of EXAMPLE 1 Formulation

| PK Parameters | Vanco | Genta C1a | Genta C1 | Genta C2/C2a | Genta Total | Vanco AUC/MIC | Genta $C_{max}$/MIC |
|---|---|---|---|---|---|---|---|
| $C_{max}$ (µg/ml) | 0.702 | 0.278 | 1.063 | 0.746 | 2.085 | | 0.3 |
| $T_{max}$ (hr) | 2 | 1 | 1 | 1 | 1 | | |
| AUC (hr * µg/ml) | 11.60 | 3.44 | 14.13 | 9.85 | 27.42 | 15.5 | |
| $T_{1/2}$ (hr) | 39.16 | 10.50 | 23.24 | 23.83 | 22.91 | | |

TABLE 9

Rabbit Tissue PK Parameters Of EXAMPLE 1 Formulation

| PK Parameters | Vanco | Genta C1a | Genta C1 | Genta C2/C2a | Genta Total | Vanco AUC/MIC | Genta $C_{max}$/MIC |
|---|---|---|---|---|---|---|---|
| $C_{max}$ (µg/ml) | 3.73 | 1.0525 | 5.865 | 3.23 | 10.1475 | | 1.3 |
| $T_{max}$ (hr) | 72 | 72 | 72 | 72 | 72 | | |
| AUC (hr * µg/ml) | 354.88 | 104.28 | 573.10 | 324.86 | 1002.25 | 473.2 | |
| $T_{1/2}$ (hr) | 35.32 | 50.32 | 49.68 | 51.60 | 50.35 | | |

Example 8: Pharmacokinetic Studies in Rabbits

New Zealand white rabbits were used to conduct pharmacokinetic ("PK") studies to evaluate the delivery of the formulations made in accordance with this invention. Two formulations were made in accordance with the procedures as set forth in EXAMPLE 1 and EXAMPLE 6, respectively, and administered into a surgical wound or subcutaneous pocket. Table 7 below shows the Rabbit PK study design in more detail:

TABLE 7

| Study | Gel Formulation | Vanco Dose (mg/kg) | Genta Dose (mg/kg) | Body Wt (kg) | Inj. Vol. (ml) | Vanco Con. (mg/g) | Genta Conc. (mg/g) |
|---|---|---|---|---|---|---|---|
| 1st experiment | EXAMPLE 1 | 2.06 | 3.08 | 2.5 | 2.0 | 2.57 | 3.85 |
| 2nd experiment | EXAMPLE 6 | 12.6 or 25.2 | 11.5 or 22.9 | 3.0 | 2 or 4 | 18.76 | 16.75 |

In a first experiment, two New Zealand white rabbits were tested. After wound instillation of the formulation of In a second experiment, six New Zealand rabbits (Group I) were tested by wound instillation of the formulation of EXAMPLE 6 containing the dose of 12.6 mg/kg of vancomycin and 11.46 mg/kg of gentamicin; and six additional New Zealand rabbits (Group II) were tested by wound instillation of the formulation of EXAMPLE 6 containing the dose of 25.2 mg/kg of vancomycin and 22.9 mg/kg of gentamicin.

The lower concentration (Group I) gel averaged 4 µg/g for both vancomycin and gentamicin total in the wound site, while the higher concentration gel (Group II) averaged and 19.4 µg/g for vancomycin and gentamicin, respectively, which are greater than four times MIC (minimum inhibitory concentration) values. Plasma concentrations of vancomycin and gentamicin from the MPI study of the formulation of EXAMPLE 6 exhibited vancomycin AUC/MIC (area under the concentration curve/minimum inhibitory concentration) ratios greater than 400 at both doses and gentamicin Cmax/MIC (maximum concentration/minimum inhibitory concentration) ratios greater than 800 at both doses.

Figure 8:
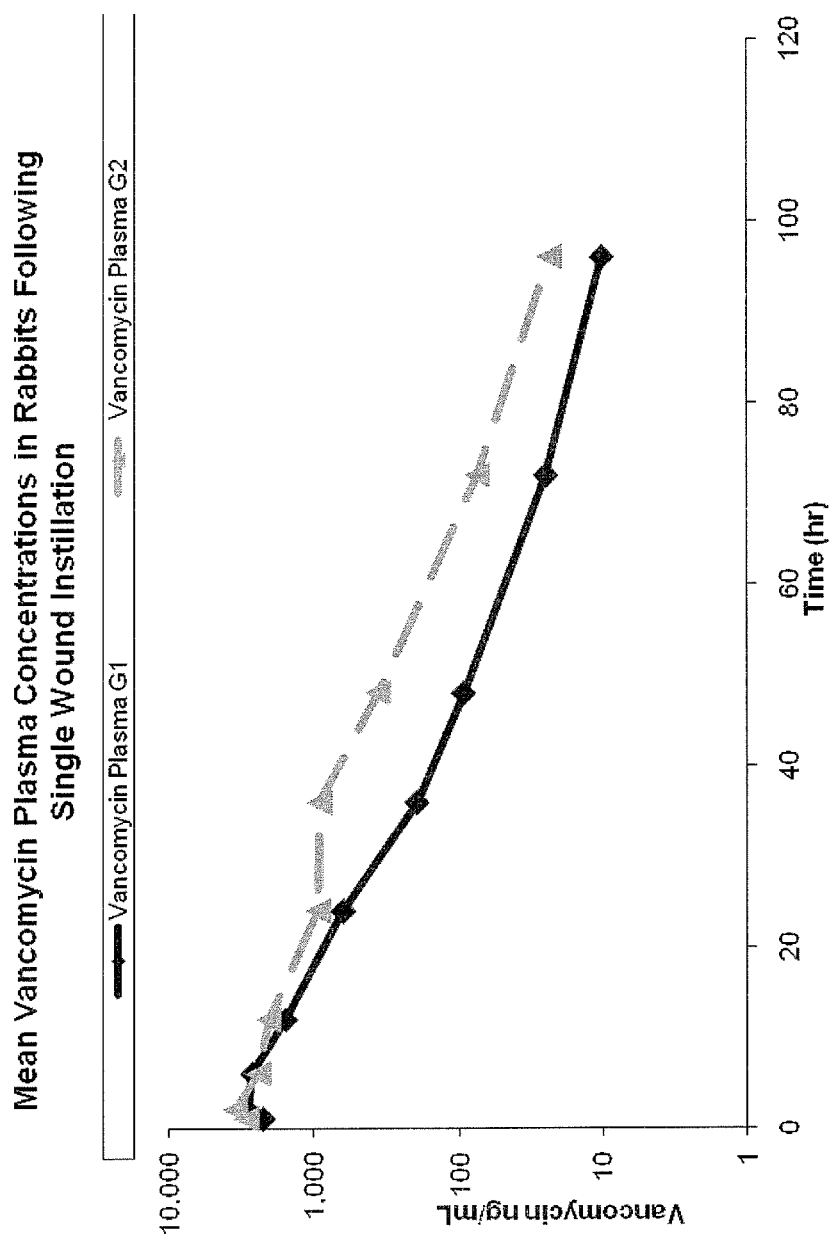
FIG. 8 illustrates mean vancomycin plasma concentrations in rabbits after single SC wound instillation of the formulation of EXAMPLE 6.
Figure 9:
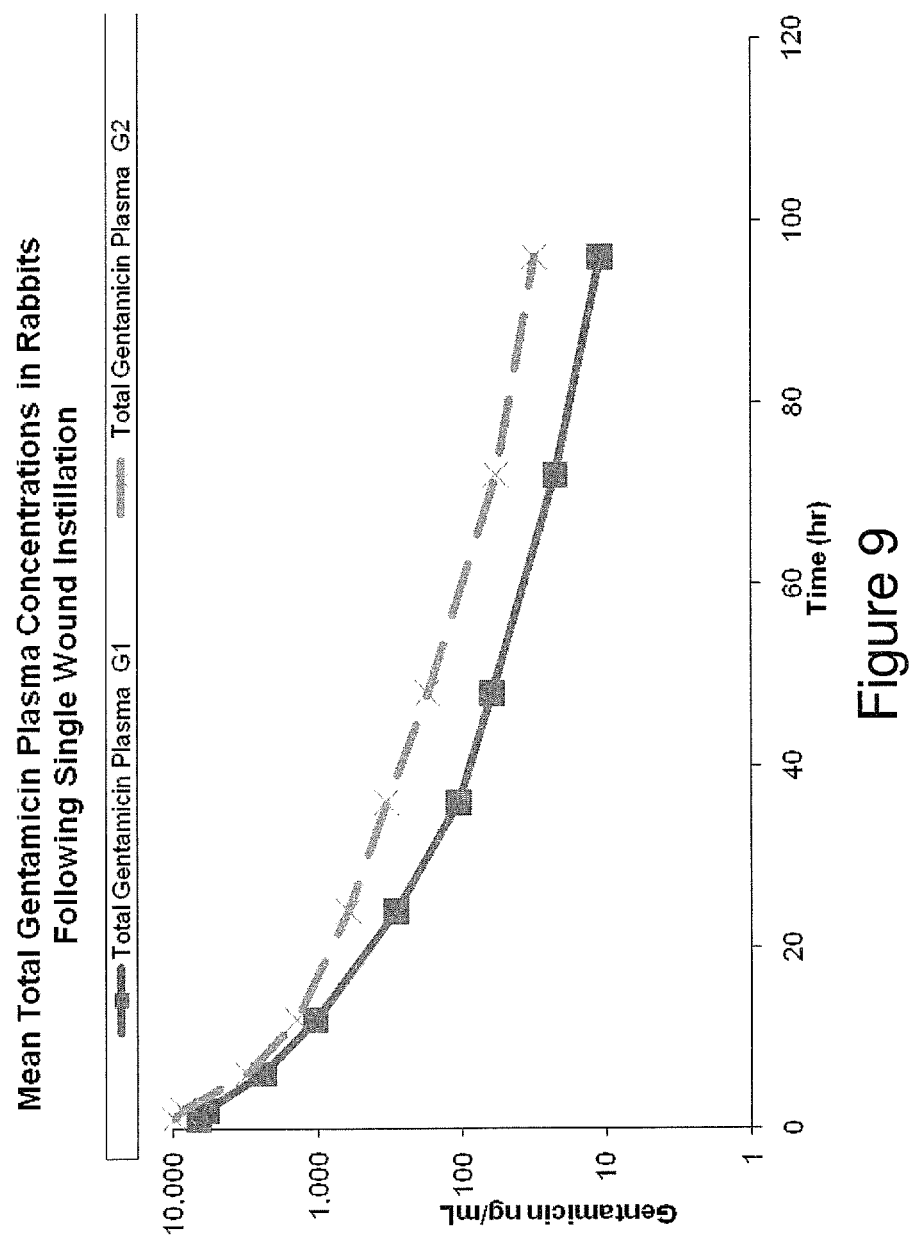
FIG. 9 illustrates mean total plasma concentration of gentamicin of the formulation of EXAMPLE 6 in rabbits.

FIG. 8 illustrates mean vancomycin plasma concentrations in rabbits after single subcutaneous (SC) wound instillation and FIG. 9 illustrates mean total gentamicin plasma concentration in rabbits.

Plasma and tissue analysis was performed by LC-MS/MS analysis, and the PK results of the formulation of EXAMPLE 6 are summarized in Table 10 below:

TABLE 10

| | Vanco | | Genta C1 | | Genta C1a | | Genta C2 + C2a Grp | | Total Genta | | Vanco | | Total Genta | |
|---|---|---|---|---|---|---|---|---|---|---|---|---|---|---|
| | 1 | 2 | 1 | 2 | 1 | 2 | 1 | 2 | 1 | 2 | AUC/MIC | | $C_{max}$/MIC | |
| | Mean | Mean | Mean | Mean | Mean | Mean | Mean | Mean | Mean | Mean | 1 | 2 | 1 | 2 |
| $C_{max}$ | 3125 | 3150 | 2737 | 3586 | 769 | 1023 | 3188 | 4318 | 6679 | 8927 | | | 835 | 1116 |
| $T_{max}$ | 3 | 2 | 1 | 1 | 1 | 1 | 1 | 1 | 1 | 1 | | | | |
| AUC last | 47392 | 60114 | 19216 | 25447 | 5463 | 7351 | 23286 | 31652 | 47966 | 64451 | 63190 | 80151 | | |

The key difference between the formulation of EXAMPLE 6 (high strength) and the formulation of EXAMPLE 1 (lower strength) is that although the PK profiles of these two formulations in small animals, such as mice, were similar, there was a greater difference in performance when tested on larger animals, such as rabbits, since the tissue concentrations for the formulation of EXAMPLE 1 fell below the 4 times MIC value sooner, therefore describing a lower area under the concentration curve (AUC) with respect to the time/area spent 4 times over the MIC.

Comparative Example 1

| Ingredients | Weight % |
|---|---|
| Gentamicin sulfate | 3 |
| Vancomycin hydrochloride | 2 |
| Phospholipon 90G | 63 |
| Sesame oil | 27 |
| Ethanol | 5 |
| TOTAL | 100.00 |

Comparative Example 1 was produced using the same methods as Examples 1 or 6, except that the homogenization, ethanol removal and/or pre-filtration steps were not performed.

Comparative Example 1 formed an opaque hard paste after lyophilization and was not clear and not filterable after adding viscosity modifying agent (ethanol).

Example 9

This Example further illustrates a process for making a depot formulation of this invention.

TABLE 11

List Of Ingredients Of A Formulation In Accordance With The Present Invention

| Component | w/w % |
|---|---|
| Gentamicin sulfate | 2.67* |
| Vancomycin hydrochloride | 1.83** |
| Soy lecithin (PL90G) | 50.0 |
| Ethanol | 6.0 |
| Sesame oil | 39.50 |
| 1N HCl | Enough to adjust to pH of 3.3 +/− 0.2 |

*Equivalent to 16.75 mg/g gentamicin
**Equivalent to 18.76 mg/g vancomycin

Gentamicin sulfate, vancomycin hydrochloride, PL90G and sesame oil and water was added to a beaker, mixed and homogenized by a high shear mixer at 500 RPM for 30 minutes to obtain a primary emulsion. The pH of the primary emulsion was then adjusted to 3.3 by 1N HCl.

A microfluidizer (M-110EH, Microfluidics Corp) was applied to reduce the droplet size of the primary emulsion. The operating pressure was set up at 25000 psi. After 6 passes, the droplet size (Z-Ave) of monophasic solution was less than 80 nm by laser light scattering scatter (Nano-ZS, Malvern). The pH of the monophasic solution was checked and adjusted to 3.3 as needed.

The monophasic solution was transferred on a stainless steel container with a filling height less than 3 cm and then lyophilized to remove water to less than 1% residual water (by Karl Fisher titration) to obtain a dry paste. After lyophilization, the dry paste was collected into a 2 L beaker. Dehydrated alcohol was added into the paste to final 25% (w/w). The mixture was dissolving by stirring at room temperature to form a clear yellow solution.

The clear solution was evaporated to reduce the alcohol content by nitrogen gas blowing to obtain a viscous and clear depot with 6% alcohol (w/w). Then the depot was sterilized by passing through two 0.2 μm SARTOPORE® 2 filters.

Comparative Example 2: Formulation Made without the Step of Microfluidization

A primary emulsion was prepared in the same way as described in Example 9. This primary emulsion was further shaken overnight or homogenized with additional high shear mixing at 5000 RPM for 2 hours, and then lyophilized in the same way as described in Example 9. For this example, a step of microfluidization was not employed. After lyophilization, dehydrated alcohol was added into the paste so that the amount of the dehydrated alcohol was about 25% (w/w). The resulting mixture was not clear even after stirring or heating for an extended period of time. The process could not be continued because a clear or filterable solution was not obtained.

Comparative Example 3: Formulation Made Using a Non-Stainless Steel Container for Lyophilization A primary emulsion and monophasic solution were prepared in the same way as described in Example 9. The nanoemulsion was lyophilized in the same way as described in Example 9 except a glass container instead of a stainless steel container was used. After lyophilization, dehydrated alcohol was added into the dry paste so that the amount of the dehydrated alcohol is about 25% (w/w) relative to the total weight of the resulting viscosity modified solution. The resulting mixture was not clear even after stirring or heating for an extended period of time. The process could not be continued because a clear or filterable solution was not obtained.

Comparative Example 4: Formulation Made without Adding Dehydrated Alcohol to about 25% (w/w)

A primary emulsion, monophasic solution and dry paste were prepared in the same way as described in Example 9. After lyophilization, dehydrated alcohol was added into the paste so that the amount of the dehydrated alcohol is about 6% (w/w) relative to the total weight of the resulting viscosity modified solution, and not 25% w/w. The resulting mixture was hazy and not clear even after stirring or heating for an extended period of time.

As mentioned above, the clearness of the solution is measured by appearance, e.g., that it is free from visually suspended particle, and the intermediate solution has a light transmittance of greater than about 90% measured at 800 nm (T800) in a 1 cm path quartz cuvette and alcohol as blank when measured by a UV-visible spectrophotometer, such as the one made by Pharmacia, Model Ultrospec III

Examples 10A-10F

| Components | Example 10A | Example 10B | Example 10F |
|---|---|---|---|
| Gentamicin sulfate | In an amount equivalent to 1.68% (w/w) gentamicin in USP assay | In an amount equivalent to 1.68% (w/w) gentamicin in USP assay | 0 |
| Vancomycin hydrochloride | In an amount equivalent to 1.88% (w/w) gentamicin in USP assay | 0 | 0 |
| Soy lecithin | 50.00 | 51.00 | 50.00 |
| Dehydrated alcohol | 6.00 | 6.00 | 6.00 |
| Sesame oil | Add to 100 | Add to 100 | Add to 100 |

Example 10A identified above was prepared according to the method of the present invention.

Example 10B identified above was also prepared according to the method of the present invention.

Example 10C identified above was prepared according to the method of present invention without containing any hydrophilic water-soluble pharmaceutically active agent.

Example 10D was prepared by mixing the formulation of Example 10C with gentamicin sulfate and vancomycin hydrochloride. Example 10D therefore was not prepared according to the method of the present invention.

Example 10E was prepared by mixing the formulation of Example 10C with gentamicin sulfate only. Example 10E therefore was not prepared in accordance with the present invention.

Example 10F was prepared without the step of microfluidization step. Accordingly, Example 10F also was not prepared in accordance with the present invention. Omission of the fluidization step resulted in precipitation in the depot. The resulting depot, therefore, was not clear.

Example 11: Structural Characterization by Small Angle X-Ray Diffraction (SAXS) of Examples 10A-10F Procedure: Small angle X-ray scattering (SAXS) data were collected in a helium chamber using a Bruker M18XHF22 rotating anode generator operating at 50 kV and 50 mA supplying a CuKα (λ=1.541838 Å) radiation beam that was collimated using a pinhole collimator. Kβ radiation was filtered out with a Ni filter. A Highstar multiwire detector was used to collect the data. The samples were loaded without modification into 0.9 mm borosilicate glass capillaries and sealed with epoxy. The samples were mounted in the He chamber on an automated goniometer at sample to detector distance of 64.55 cm. To prevent scatter from air He gas was purged into the chamber for 1 hour and then each sample was collected for 7200 seconds. The data were smoothed and integrated over the 360°χ circle from 0.8 to 4.7° 2θ in 0.1 and 0.02 degree widths. The patterns were compared and the 0.1 degree width integrations were used for the refinements of peak positions.

Figure 12:
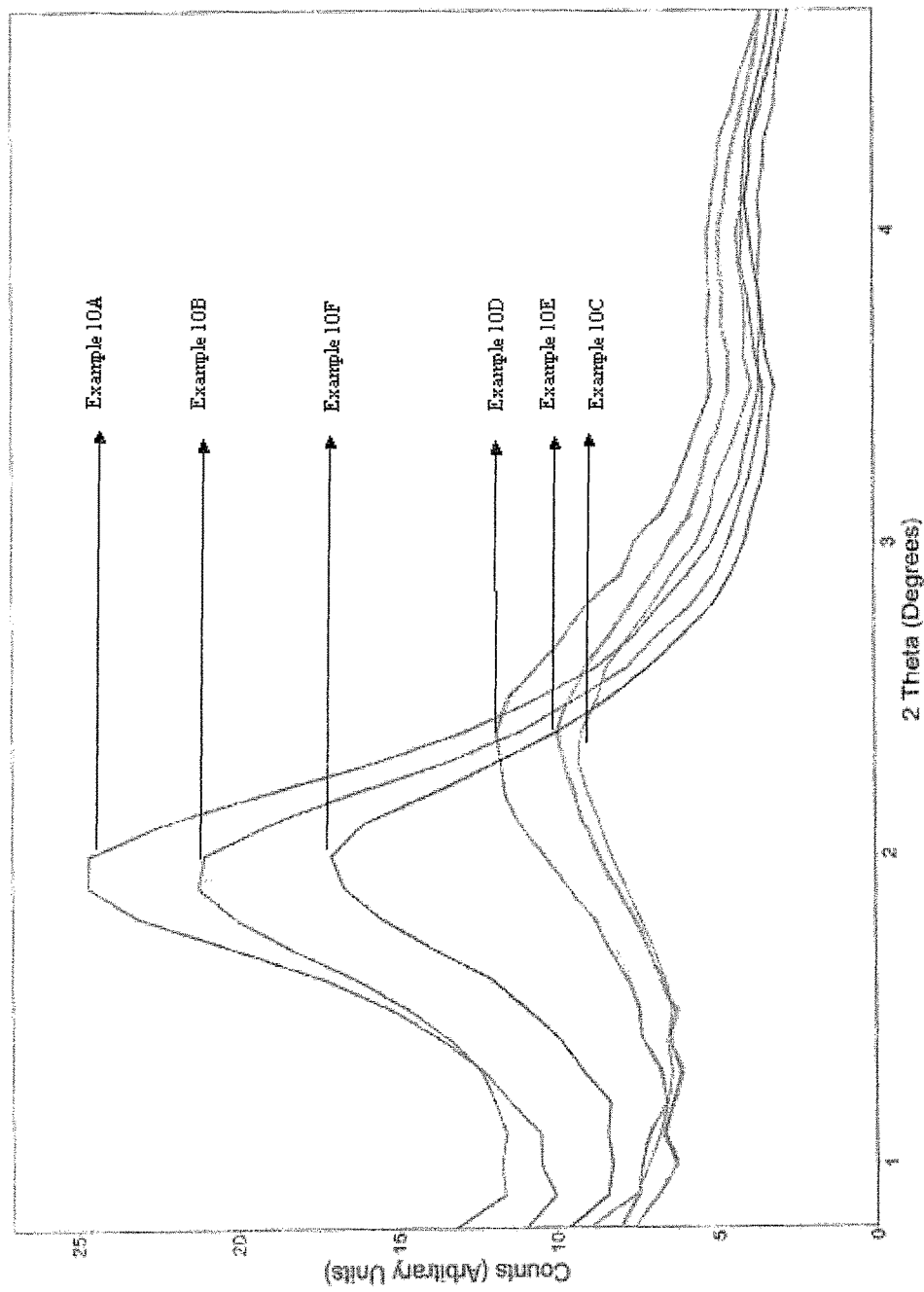
FIG. 12 illustrates the small angle X-ray diffraction (SAXS) patterns of Examples 10A to 10F.

Results: FIG. 12 illustrates the small angle X-ray diffraction (SAXS) patterns of Examples 10A-10F. Two distinct diffraction peaks were observed. Examples 10A, 10B and 10F exhibited at low angles diffraction peak at about 2 Theta (degree) and the two physical mixtures (Examples 10D and 10E) and the depot vehicle without any active agent (Example 10C) showed a much broader diffraction peak at about 2.5 Theta (degree).

The formulations produced using the method of the present invention (Examples 10A and 10B) had a unique SAXS diffraction peak formed at about 2 Theta (degree), which was not found in Example 10C or physical mixtures of the depot vehicle with the same drugs (Examples 10D and 10E). Example 10C has smaller lattice spacing than Examples 10A, 10B and 10F.

There is approximately 8-9 Å increase calculated in the lattice spacing when gentamicin and vancomycin are incorporated into the depot in accordance with the present invention, forming such unique structure (herein referred to as the "2-Theta Structure").

The two physical mixtures (Examples 10D and 10E) showed lattice spacing of the primary diffraction peak that was consistent with depot vehicle (Example 10C), indicating the physical mixing of the depot vehicle with gentamicin and vancomycin does not change the structure of the vehicle.

It is only after the vancomycin and/or gentamicin are incorporated into the depot vehicle using the process of the present invention that the 2-Theta Structure is formed.

This clearly indicates that the compositions of the present invention have a unique 2-Theta Structure and such structure can only be obtained by using the method of preparation of the present invention.

The reduced diffraction intensity at 2 Theta (degree) observed for Example 10F suggests that there exists partially the "2-Theta Structure" in the composition prepared without the microfluidization step.

Conclusion: The compositions of the present invention, Examples 10A and 10 B contain uniquely different 2-Theta Structure.

Example 12: Structural Characterization by Thermal Gravimetric Analysis (TGA) of Examples 10A and 10D Procedure: TGA experiments were carried on a Seiko Instruments TG/DTA 220 nit. Temperature and enthalpy were calibrated using Indium and Tin standards. Scans were completed using a rate of 10° C./min from 25-300° C. with a nitrogen purge rate of 80 ml/min in open pans and a sample size between 5 and 10 mg.

Figure 13:
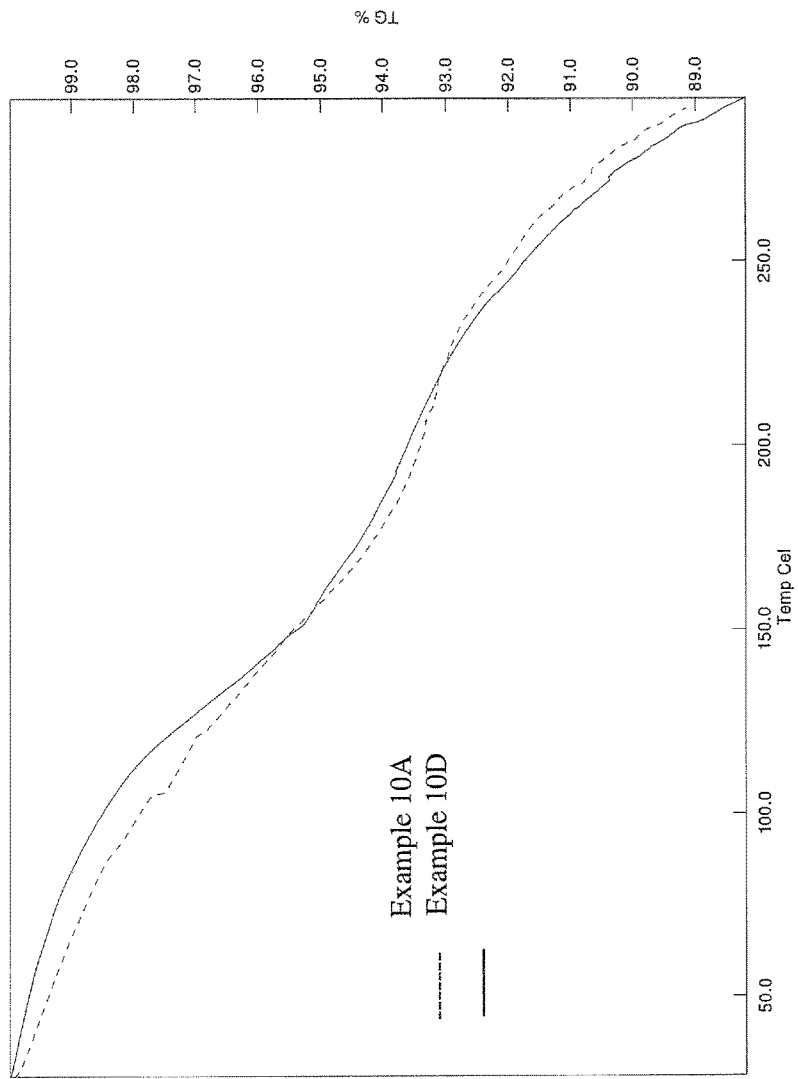
FIG. 13 illustrates the thermal gravimetric analysis of Examples 10A and 10D

Results: As shown in FIG. 13, the TGA results showed small difference in weight loss profile between Example 10A which was prepared according to the method of the present invention and Example 10D, which was not prepared according to the method of the present invention.

Example 13: Structural Characterization by Differentiating Scanning Calorimetry (DSC) of Examples 10A and 10D Procedure: DSC experiments were carried using a Seiko Instruments DSC 120 single cell Modulated DSC with RSC (refrigerated cooling) unit. The DSC was calibrated for temperature and cell constant by using an Indium standard. Scans were run in normal DSC mode at a rate of 10° C./min in sealed pans with a Nitrogen purge rate of 40 ml/min with weights between 5 and 10 mg used for each sample. Scans were run from 25-300° C.

Results: As shown in FIG. 14, the DSC profiles for both samples (Example 10A and 10D) are characterized by a major endothermic event up to about 100° C., which is likely related to desolvation of the samples. Example 10D, however, exhibited an additional endothermic peak at about ° C., possibly due to melting of a solid drug, i.e., gentamicin sulfate and/or vancomycin hydrochloride.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for making a depot comprising:
   (a) forming an oil-in-water emulsion including a phospholipid, an oil, at least one hydrophilic water-soluble pharmaceutically active agent selected from the group consisting of vancomycin, gentamicin, a pharmaceutically acceptable salt thereof and a mixture thereof and water;
   (b) converting the emulsion to a monophasic solution having a pH of between about 3 to about 6;
   (c) lyophilizing the monophasic solution to obtain a dry paste,
   (d) adding a viscosity modifying agent to the dry paste in an amount sufficient to obtain a viscosity modified solution,
   (e) removing at least some of the viscosity modifying agent to obtain a depot, and
   (f) sterilizing the depot, wherein the water present in the depot is no more than about 4 wt % relative to the total weight of the depot.

2. The method of claim 1, wherein the depot is clear.

3. The method of claim 1, wherein the depot is ultra clear.

4. The method of claim 1, wherein said step of forming the oil-in-water emulsion comprises: dissolving the at least one hydrophilic water-soluble pharmaceutically active agent selected from the group consisting of vancomycin, gentamicin, a pharmaceutically acceptable salt thereof and a mixture thereof in the water to obtain an aqueous solution; and mixing the aqueous solution with the phospholipid and the oil.

5. The method of claim 1, wherein the amount of the viscosity modifying agent in the depot is from about 2 wt % to about 18 wt % relative to the total weight of the depot.

6. The method of claim 1, wherein the at least one hydrophilic water-soluble pharmaceutically active agent is vancomycin hydrochloride and gentamicin sulfate.

7. The method of claim 1, wherein the viscosity modifying agent is ethanol.

8. A depot produced in accordance with a method comprising:
   (a) forming an oil-in-water emulsion including a phospholipid, an oil, at least one hydrophilic water-soluble pharmaceutically active agent selected from the group consisting of vancomycin, gentamicin, a pharmaceutically acceptable salt thereof and a mixture thereof and water;
   (b) converting the emulsion to a monophasic solution having a pH of between about 3 to about 6;
   (c) lyophilizing the monophasic solution to obtain a dry paste;
   (d) adding a viscosity modifying agent to the dry paste in an amount sufficient to obtain a viscosity modified solution;
   (e) removing at least some of the viscosity modifying agent to obtain a depot; and
   (f) sterilizing the depot, wherein the water present in the depot is no more than about 4 wt % relative to the total weight of the depot.

9. The depot of claim 8, wherein the depot is clear.

10. The depot of claim 8, wherein the depot is ultra clear.

11. The depot of claim 8, wherein said step of forming the oil-in-water emulsion comprises: dissolving the at least one hydrophilic water-soluble pharmaceutically active agent selected from the group consisting of vancomycin, gentamicin, a pharmaceutically acceptable salt thereof and a mixture thereof in the water to obtain an aqueous solution; and mixing the aqueous solution with the phospholipid and the oil.

12. The depot of claim 8, wherein the amount of the viscosity modifying agent in the depot is from about 2 wt % to about 18 wt % relative to the total weight of the depot.

13. The depot of claim 8, wherein the at least one hydrophilic water-soluble pharmaceutically active agent is vancomycin hydrochloride and gentamicin sulfate.

14. The depot of claim 8, wherein the viscosity modifying agent is selected from the group consisting of ethanol, isopropanol, and a mixture thereof.

15. A depot comprising a hydrophilic water-soluble pharmaceutically active agent selected from the group consisting of vancomycin, gentamicin, a pharmaceutically acceptable salt thereof, and a mixture thereof water; a phospholipid; an oil; and a viscosity modifying agent; wherein the water present in the depot is no more than about 4 wt % relative to the total weight of the depot and the viscosity of the depot is from about 100 centipoise to about 5000 centipoise.

16. The depot of claim 15, wherein the amount of the viscosity modifying agent present in the depot is from about 1 wt % to about 20 wt % relative to the total weight of the depot.

17. The depot of claim 15, wherein the viscosity modifying agent is selected from the group consisting of ethanol, isopropanol, and a mixture thereof.

18. The depot of claim 15, wherein the depot is clear.

19. The method of claim 15, wherein the depot is ultra clear.

20. A method of administering the depot of claim 15 to a patient in need thereof via intradermal, intraincisional, intramuscular, subcutaneous, instillation or topically wherein the depot is sufficient to release the pharmaceutically active agent for a period of about at least one day with a dosing volume from about 0.1 mL to about 100 mL.

21. A method of treating surgical site infection by introducing the depot of claim 15 wherein the depot is sufficient to release the pharmaceutically active agent for a period of about at least one day with a dosing volume from about 0.1 mL to about 100 mL.

22. A depot comprising at least one hydrophilic water-soluble pharmaceutical active agent selected from the group comprising vancomycin, gentamicin, a pharmaceutically acceptable salt thereof, or mixtures thereof; water; a phospholipid; an oil; optionally pH adjusting agent; and a viscosity modifying agent; wherein the depot is administered via intradermal, intraincisional, intramuscular, subcutaneous, instillation or topically and provides high local tissue concentrations and low systemic concentrations of vancomycin and/or gentamicin.

23. The depot of claim 22, wherein the depot is administered for preventing and/or treating infection.

24. The depot of claim 22, wherein the depot is administered for preventing and/or treating surgical site infection.

25. The depot of claim 22, wherein the depot is rendering localized tissue unable to sustain pathogenic microorganisms at wound.

26. The depot of claim 22, wherein the depot comprising gentamicin and provides systemic concentration of gentamicin less than about 10 mg/l.

27. The depot of claim 22, wherein the depot does not cause toxicity to kidney and/or other organs.

28. The depot of claim 22, wherein the amount of the viscosity modifying agent present in the depot is from about 1 wt % to about 20 wt % relative to the total weight of the depot.

29. The depot of claim 22, wherein the viscosity modifying agent is selected from the group consisting of ethanol, isopropanol, and a mixture thereof.

30. A method of treating surgical site infection by introducing the depot of claim 22 wherein the depot is sufficient to release the pharmaceutically active agent for a period of about at least one day with a dosing volume from about 0.1 mL to about 100 mL.

31. A method of treating a wound infection comprising administering to said wound the depot of claim 15.

32. A method of treating a wound infection comprising administering to said wound the depot of claim 22.

33. The method of claim 32, wherein the method renders localized tissue unable to sustain pathogenic microorganisms by administering a depot of the present invention to the wound.

34. The method of claim 33, wherein the wound infection is surgical site infection.

35. The method of claim 32, wherein the method provides sufficiently high tissue concentration to treat and/or prevent infections at a local site.

36. The method of claim 32, wherein the method does not cause toxicity to kidney and/or other organs.

37. The method of claim 32, wherein the depot is sufficient to release the pharmaceutically active agent for a period of about at least one day with a dosing volume from about 0.1 mL to about 100 mL.

38. The method of claim 32, wherein the depot comprising gentamicin, provides systemic concentration of gentamicin less than about 10 mg/l.

39. A method of treating a wound infection comprising administering to said wound a depot comprising: at least one hydrophilic water-soluble pharmaceutically active agent selected from group consisting of vancomycin, gentamicin, and pharmaceutically acceptable salts thereof; water; a phospholipid; an oil; and a viscosity modifying agent; wherein the water present in the depot is no more than about 4 wt % relative to the total weight of the depot.

40. The method of claim 39, wherein the method renders localized tissue unable to sustain pathogenic microorganisms by administering a depot of the present invention to the wound.

41. The method of claim 40, wherein the wound infection is surgical site infection.

42. The method of claim 39, wherein the method provides sufficiently high tissue concentration to treat and/or prevent infections at a local site.

43. The method of claim 39, wherein the method does not cause toxicity to kidney and/or other organs.

44. The method of claim 39, wherein the depot is sufficient to release the pharmaceutically active agent for a period of about at least one day with a dosing volume from about 0.1 mL to about 100 mL.

45. The method of claim 39, wherein the depot comprising gentamicin, provides systemic concentration of gentamicin less than about 10 mg/l.

* * * * *

UNITED STATES PATENT AND TRADEMARK OFFICE
CERTIFICATE OF CORRECTION

PATENT NO. : 9,682,040 B2
APPLICATION NO. : 15/347949
DATED : June 20, 2017
INVENTOR(S) : Hailiang Chen et al.

Page 1 of 1

It is certified that error appears in the above-identified patent and that said Letters Patent is hereby corrected as shown below:

On the Title Page

(73) Assignee, delete "Dr. Reddy's Laboratories Ltd." and replace with "Dr. Reddy's Laboratories SA"

In the Claims

Claim 15, Column 30, Line 45, replace "thereof water" with "thereof; water"

Signed and Sealed this
Eighth Day of August, 2017

Joseph Matal
*Performing the Functions and Duties of the*
*Under Secretary of Commerce for Intellectual Property and*
*Director of the United States Patent and Trademark Office*